(12) United States Patent
Ono et al.

(10) Patent No.: US 7,094,448 B2
(45) Date of Patent: Aug. 22, 2006

(54) SPRAY PACK

(75) Inventors: Hirofumi Ono, Numazu (JP); Hideki Amakawa, Fuji (JP)

(73) Assignee: Asahi Kasei Chemical Corporation, Tokyo (JP)

( * ) Notice: Subject to any disclaimer, the term of this patent is extended or adjusted under 35 U.S.C. 154(b) by 368 days.

(21) Appl. No.: 10/330,920

(22) Filed: Dec. 27, 2002

(65) Prior Publication Data

US 2004/0123775 A1    Jul. 1, 2004

(51) Int. Cl.
*B05D 1/00* (2006.01)
*C09D 1/00* (2006.01)
*C09D 101/02* (2006.01)
*C08B 16/00* (2006.01)
*C07H 1/00* (2006.01)

(52) U.S. Cl. ............... 427/427.4; 106/15.05; 106/162.9; 106/163.01; 106/200.3; 106/203.1; 106/204.01; 106/204.3; 424/43; 424/46; 424/47; 424/59; 424/71; 424/401; 424/407; 514/781; 536/1.11; 536/56; 536/57; 536/123.1; 536/123.12; 536/124; 536/126

(58) Field of Classification Search ......... 106/15.05, 106/162.9, 163.01, 200.3, 203.1, 204.01, 106/204.3; 424/401, 407, 43, 46, 47, 59, 424/71; 514/781; 536/56, 57, 1.11, 123.12, 536/126, 123.1, 124
See application file for complete search history.

(56) References Cited

U.S. PATENT DOCUMENTS

| | | | | |
|---|---|---|---|---|
| 3,258,354 A | * | 6/1966 | Battista | 106/163.01 |
| 4,260,082 A | * | 4/1981 | Rooney et al. | 222/340 |
| 5,335,824 A | * | 8/1994 | Weinstein | 222/82 |
| 5,370,118 A | * | 12/1994 | Vij et al. | 600/422 |
| 5,520,963 A | * | 5/1996 | Liu | 427/388.1 |
| 6,541,627 B1 | * | 4/2003 | Ono et al. | 536/56 |
| 6,755,357 B1 | * | 6/2004 | Duqueroie et al. | 239/327 |
| 2004/0127605 A1 | * | 7/2004 | Redding | 523/500 |
| 2004/0208998 A1 | * | 10/2004 | Steininger et al. | 427/372.2 |
| 2006/0027280 A1 | * | 2/2006 | Heatley et al. | 141/9 |

FOREIGN PATENT DOCUMENTS

| | | |
|---|---|---|
| EP | 1 036 799 A1 | 9/2000 |
| JP | 9-241115 | 9/1997 |
| JP | 2000-51682 A | 2/2000 |
| JP | 2000-229255 A | 8/2000 |
| JP | 2000-351726 | 12/2000 |
| JP | 2001-72999 A | 3/2001 |
| JP | 2001-89359 A1 | 4/2001 |

* cited by examiner

*Primary Examiner*—David Brunsman
(74) *Attorney, Agent, or Firm*—Dickstein, Shapiro, Morin & Oshinsky, LLP.

(57) ABSTRACT

Disclosed is a spray pack for use in forming a uniform, stable spray coating, comprising a spray container device and, packed therein, a spraying composition comprising a liquid dispersion medium and, dispersed therein, particulate cellulose having an average degree of polymerization (DP) of not more than 300 and an average particle diameter of not more than 10 μm, wherein the composition has a cellulose content of from 0.1 to 5.0% by weight, and wherein the composition exhibits a maximum viscosity value ($\eta_{max}$) of $1 \times 10^3$ mPa·s or more in the viscosity-shear stress curve obtained, with respect to the composition, using a cone-plate type rotating viscometer in a shear rate region of from $1 \times 10^{-3}$ s$^{-1}$ to $1 \times 10^2$ s$^{-1}$ and at 25° C. A method for forming a uniform, stable spray coating by using the above-mentioned spray pack is also disclosed.

20 Claims, 3 Drawing Sheets

SPRAY PACK

BACKGROUND OF THE INVENTION

1. Field of the Invention

The present invention relates to a spray pack for use in forming a uniform, stable spray coating, comprising a spray container device and, packed therein, a spraying composition comprising a liquid dispersion medium and, dispersed therein, particulate cellulose having an average degree of polymerization (DP) of not more than 300 and an average particle diameter of not more than 10 µm, wherein the spraying composition has a cellulose content of from 0.1 to 5.0% by weight, and wherein the spraying composition exhibits a maximum viscosity value ($\eta_{max}$) of $1\times10^3$ mPa·s or more in the viscosity-shear stress curve obtained, with respect to the composition, using a cone-plate type rotating viscometer in a shear rate region of from $1\times10^{-3}$ s$^{-1}$ to $1\times10^2$ s$^{-1}$ and at 25° C. The spraying composition used in the spray pack of the present invention is advantageous not only in that it has excellent spraying properties and also in that, after the spraying, the sprayed composition (coating) has excellent properties with respect to fixation to the surface coated, anti-dripping properties, spreadability and finish (uniformity of the coating). Therefore, the present invention is also concerned with a method for forming a uniform, stable spray coating, which comprises providing a spray pack comprising a spray container device and, packed therein, a spraying composition of the above-mentioned type; and actuating the spray container device to spray the spraying composition onto a surface, thereby forming a spray coating on the surface.

2. Prior Art

In recent years, spraying products are used in a wide variety of fields, such as the fields of skincare products, hair care products, a medicine for external use, a medicine for oral use, an insecticide, a fragrance, a deodorizer, an antimicrobial agent, a sterilizer, a halitosis deodorizer, a detergent, a paint, a coating agent for anti-fogging treatment, a coating agent for anti-static treatment, and an antiseptic agent. A spraying product comprises a spray container device and, packed therein, a spraying composition. In most cases, the spraying composition packed in the spray container device is in liquid form.

A spraying composition is desired to have the following properties: (1) a general purpose container can be used as the spray container device therefor, and good spraying can be performed in a wide variety of environments; (2) after the spraying, the sprayed composition has excellent properties with respect to fixation to the surface coated and the uniformity of the coating; (3) the sprayed composition is unlikely to drip even when the surface coated is vertical or inclined; and (4) when the sprayed composition is dried, a coating can be formed which is not only stable but also has high safety in that skin stimulation (i.e., skin irritation) and the like are not exhibited. However, there is no conventional spraying composition possessing all of these desired properties.

In order to solve the problems of the conventional spraying compositions, various proposals have been made.

For example, in order to solve the tasks (1) to (3) above, Unexamined Japanese Patent Application Laid-Open Specification No. 2001-89359 proposes a method in which a polymeric thickening agent is added to a spraying composition, thereby increasing the viscosity of the composition. However, the following should be noted. In the case of a conventional polymer solution as a spraying composition, when the viscosity of the spraying composition is increased too much by adding a thickening agent in an attempt to prevent the dripping thereof after the spraying, it becomes impossible to spray the composition due to the high viscosity of the composition. Therefore, for enabling drawing up of the composition by suction through the suction tube to the spray nozzle and enabling the spraying of the composition, it is necessary to decrease the viscosity of the composition by some degree. However, such decrease in viscosity, in turn, results in a lowering of the anti-dripping properties of the composition. Therefore, it is very difficult to achieve a good balance of the anti-dripping properties and the sprayability (spraying properties) of the composition. Further, even if conditions can be found which enable the spraying of the composition, there has conventionally been a problem in that, due to the stringiness of the composition (characteristic of a polymer solution), the composition upon being sprayed cannot form desired fine particles (mist); that is, the mist-forming ability of the composition is poor, resulting in non-uniformity of the coating obtained, as compared to the case of a spraying composition which does not contain a thickening agent.

Further, in order to solve the tasks (2) and (3) above, many methods have been proposed, for example, a method in which a surfactant is added to the composition so as to increase the viscosity by utilizing the interactions between the micelles formed in the aqueous phase, and a method in which the surface tension of the sprayed composition (liquid particles) on the coated surface is controlled (see, for example, Unexamined Japanese Patent Application Laid-Open Specification Nos. 2001-72999 and 2000-351726). However, there is a problem, for example, in that the compositions of these patent documents have a fluidity and therefore cannot be sprayed when the spray container device containing such a composition is held upside down. Therefore, the task (1) above cannot be completely solved by these conventional methods. Further, there are other problems, as follows. These conventional methods cannot increase the viscosity of the composition to a level sufficient for substantially completely preventing the dripping after spraying. Furthermore, when a large amount of a surfactant is added to the composition in an attempt to increase the viscosity thereof, the surfactant is likely to irritate the skin. Thus, the task (4) above (concerning safety) and the like cannot be solved.

In order to solve the tasks (1) and (3) above, improvements in the structure of the spray container device have been suggested (see, for example, Unexamined Japanese Patent Application Laid-Open Specification No. 2000-229255). However, this technique poses the following problems. In the case of the use of such a spray container device, when the spraying is performed for forming a thin coating, the dripping after spraying can be prevented. However, when the spraying is performed for forming a thick coating (i.e., when repeated sprayings are needed), there is a problem in that the dripping of the sprayed composition occurs. In addition, in this technique, the spray container device has a complicated structure, so that such spray container device lacks the general-purpose properties and the cost for producing the spray container device becomes markedly high. Therefore, from the viewpoint of developing a spraying composition which can be used without limitation in a wide variety of application fields, this technique cannot be considered as a fundamental solution to the problem of the dripping after spraying.

In an attempt to provide a relatively well-balanced solution to all of the tasks (1) to (4) above, Unexamined Japanese Patent Application Laid-Open Specification Nos. Hei 9-241115 and 2000-51682 disclose a gel-like, spraying composition which contains, as a main component, hectorite comprising hydrophilic smectite. However, the main component of the spraying composition is an inorganic compound which has not actually been put to use for a time long enough to confirm its safety. Further, in the case of this composition, a problem arises in that aggregation of hectorite is likely to occur in a dispersion medium (such as alcohol) which is widely used in a spraying composition, thus causing a lowering of the spraying properties. In addition, there is a problem in that dissolution-out of a large amount of salt contained in hectorite occurs, and the salt is likely to induce aggregation of other components which are sensitive to the presence of salt; this means that the freedom of formulation of the spraying composition is limited.

At the "Dai 13-kai Kobunshi Geru Kenkyu Toronkai (13th Forum on Polymer Gel)" (sponsored by the Society of Polymer Science, Japan; Jan. 17–18, 2002; pages 49–50 of the preliminary text), the present inventors reported their finding that, although an aqueous dispersion of the cellulose used in the present invention has gel-like properties (exhibiting no fluidity), it has excellent spraying properties such that it can be easily sprayed using an ordinary spray container device, thereby exhibiting good spraying. However, for utilizing such finding in a wide variety of fields of industry, it was needed to find conditions under which the gel-like, cellulose dispersion can, as well, exhibit excellent properties with respect to stability of gel and to spraying performance even when the cellulose dispersion is a composite formulation additionally containing not only an alcohol but also various types of additives.

SUMMARY OF THE INVENTION

In this situation, the present inventors have made extensive and intensive studies with a view toward solving the above-mentioned problems of the prior art. As a result, it has unexpectedly been found that a spraying composition desired for the above-mentioned object can be produced by using a cellulose dispersion which comprises a liquid dispersion medium (such as water) and, dispersed therein, particulate cellulose having a specific, relatively small particle diameter. More specifically, the present inventors have unexpectedly found that the cellulose dispersion disclosed in WO 99/28350 (corresponding to EP 1 036 799 A1) has excellent properties with respect to spraying properties; formation and maintenance of a foam; thixotropic properties (i.e., the ability to exhibit a low viscosity quickly at the application of a lower shear stress than in the case of other materials); and dispersion stability for various compounds. Further, it has surprisingly been found that a spraying composition which is obtained by adjusting the viscosity of the above-mentioned cellulose dispersion to a value within a specific range can solve all of the tasks (1) to (4) above, and such spraying composition is also advantageous in that it has high transparency and, after spraying and drying, can provide a coating having high transparency. Furthermore, it has also been found that, even when various types of liquid dispersion mediums and functional additives are added to the spraying composition, the composition is stable and exhibits excellent spraying properties. Based on these findings, the present invention has been completed.

Accordingly, it is an object of the present invention to provide a spray pack for use in forming a uniform, stable spray coating, which packs therein a spraying composition, wherein the spraying composition can solve all of the tasks (1) to (4) above, i.e., a spraying composition which has the following properties: (1) a general purpose container can be used as the spray container device therefor, and good spraying can be performed in a wide variety of environments; (2) after the spraying, the sprayed composition has excellent properties with respect to fixation to the surface coated and the uniformity of the coating; (3) the sprayed composition is unlikely to drip even when the surface coated is vertical or inclined; and (4) when the sprayed composition is dried, a coating can be formed which is not only stable but also has high safety in that skin stimulation (i.e., skin irritation) and the like are not exhibited.

It is another object of the present invention to provide a method for forming a uniform, stable spray coating by using the above-mentioned spray pack.

The foregoing and other objects, features and advantages of the present invention will be apparent from the following detailed description taken in connection with the accompanying drawings and the appended claims.

DETAILED DESCRIPTION OF THE INVENTION

Figure 1:
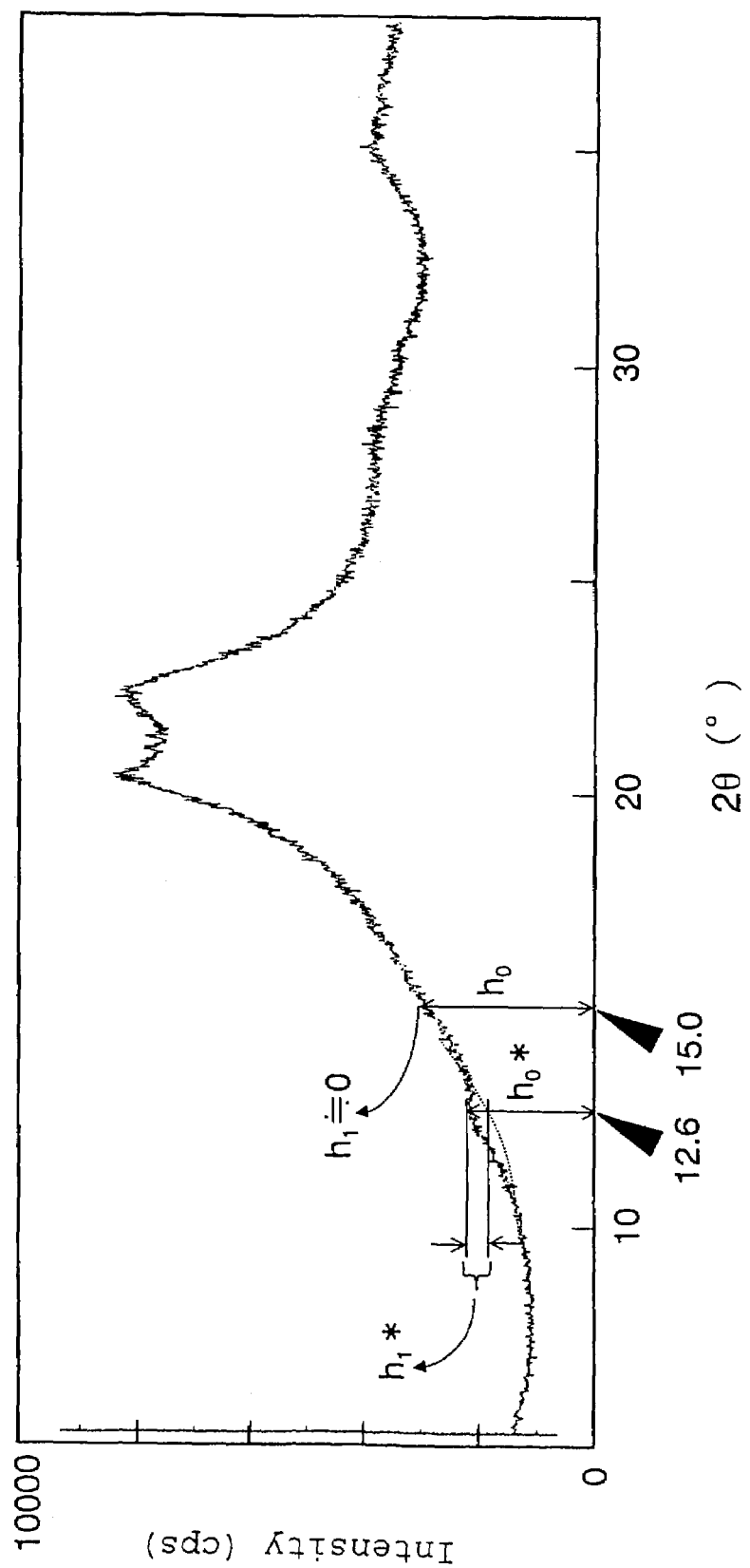
FIG. 1 is a graph showing the method for determining $h_0$, $h_1$, $h_0^*$ and $h_1^*$ in a wide-angle X-ray pattern obtained with respect to a cellulose used in the present invention (a dried product obtained from sample A)

According to the present invention, there is provided a spray pack for use in forming a uniform, stable spray coating, comprising a spray container device and, packed therein, spraying composition comprising a liquid dispersion medium and, dispersed therein, particulate cellulose having an average degree of polymerization (DP) of not more than 300 and an average particle diameter of not more than 10 µm, the spraying composition having a cellulose content of from 0.1 to 5.0% by weight, wherein the spraying composition exhibits a maximum viscosity value ($\eta_{max}$) of $1 \times 10^3$ mPa·s or more in the viscosity-shear stress curve obtained, with respect to the composition, using a cone-plate type rotating viscometer in a shear rate region of from $1 \times 10^{-3}$ s$^{-1}$ to $1 \times 10^2$ s$^{-1}$ and at 25° C.

For easy understanding of the present invention, the essential features and various preferred embodiments of the present invention are enumerated below.

1. A spray pack for use in forming a uniform, stable spray coating, comprising a spray container device and, packed therein, a spraying composition comprising a liquid dispersion medium and, dispersed therein, particulate cellulose having an average degree of polymerization (DP) of not more than 300 and an average particle diameter of not more than 10 μm, the spraying composition having a cellulose content of from 0.1 to 5.0% by weight, wherein the spraying composition exhibits a maximum viscosity value ($\eta_{max}$) of $1\times10^3$ mPa·s or more in the viscosity-shear stress curve obtained, with respect to the composition, using a cone-plate type rotating viscometer in a shear rate region of from $1\times10^{-3}$ s$^{-1}$ to $1\times10^2$ s$^{-1}$ and at 25° C.

2. The spray pack according to item 1 above, wherein the particulate cellulose has an average degree of polymerization (DP) of not more than 100, and has a cellulose I type crystal component fraction of 0.1 or less and a cellulose II type crystal component fraction of 0.4 or less, and wherein the particulate cellulose has an average particle diameter of not more than 2 μm.

3. The spray pack according to item 1 or 2 above, wherein the particulate cellulose has an average particle diameter of not more than 1 μm.

4. The spray pack according to item 1 or 2 above, wherein the maximum viscosity value ($\eta_{max}$) in the viscosity-shear stress curve is $5\times10^5$ mPa·s or more.

5. The spray pack according to item 1 or 2 above, wherein the liquid dispersion medium comprises water and an organic solvent.

6. The spray pack according to item 5 above, wherein the organic solvent is a water-soluble alcohol.

7. The spray pack according to item 1 or 2 above, which further comprises at least one functional additive.

8. The spray pack according to item 7 above, wherein at least a part of the functional additive is an ionic compound, and wherein the content of the ionic compound in the composition is from 0.1 to 10% by weight.

9. The spray pack according to item 7 above, wherein the at least one functional additive is selected from the group consisting of an oil compound, a humectant, a surfactant, a metal oxide, an ultraviolet screener, an inorganic salt, a metal powder, a gum, a dye, a pigment, a silica compound, a latex, a water-soluble polymer, an amino acid, a cosmetic ingredient, a pharmaceutical, an insecticide, a deodorizer, an antimicrobial agent, an antiseptic agent and a perfume.

10. The spray pack according to item 1 or 2 above, wherein when the spraying composition is diluted with water to have a particulate cellulose concentration of 0.05% by weight, the resultant aqueous composition exhibits a transmittance of 80% or more to visible rays having a wavelength of 660 nm.

11. A method for forming a uniform, stable spray coating, comprising:

providing a spray pack comprising a spray container device and, packed therein, a spraying composition, and actuating the spray container device to spray the spraying composition onto a surface, thereby forming a spray coating on the surface, the spraying composition comprising a liquid dispersion medium and, dispersed therein, particulate cellulose having an average degree of polymerization (DP) of not more than 300 and an average particle diameter of not more than 10 μm, the spraying composition having a cellulose content of from 0.1 to 5.0% by weight, wherein the spraying composition exhibits a maximum viscosity value ($\eta_{max}$) of $1\times10^3$ mPa·s or more in the viscosity-shear stress curve obtained, with respect to the composition, using a cone-plate type rotating viscometer in a shear rate region of from $1\times10^{-3}$ s$^{-3}$ to $1\times10^2$ s$^{-1}$ and at 25° C.

12. The method according to item 11 above, wherein the particulate cellulose has an average degree of polymerization (DP) of not more than 100, and has a cellulose I type crystal component fraction of 0.1 or less and a cellulose II type crystal component fraction of 0.4 or less, and wherein the particulate cellulose has an average particle diameter of not more than 2 μm.

13. The method according to item 11 or 12, wherein the particulate cellulose has an average particle diameter of not more than 1 μm.

14. The method according to item 11 or 12 above, wherein the maximum viscosity value ($\eta_{max}$) in the viscosity-shear stress curve is $5\times10^5$ mPa·s or more.

15. The method according to item 11 or 12 above, wherein the liquid dispersion medium comprises water and an organic solvent.

16. The method according to item 15 above, wherein the organic solvent is a water-soluble alcohol.

17. The method according to item 11 or 12 above, which further comprises at least one functional additive.

18. The method according to item 17 above, wherein at least a part of the functional additive is an ionic compound, and wherein the content of the ionic compound in the composition is from 0.1 to 10% by weight.

19. The method according to item 17 above, wherein the at least one functional additive is selected from the group consisting of an oil compound, a humectant, a surfactant, a metal oxide, an ultraviolet screener, an inorganic salt, a metal powder, a gum, a dye, a pigment, a silica compound, a latex, a water-soluble polymer, an amino acid, a cosmetic ingredient, a pharmaceutical, an insecticide, a deodorizer, an antimicrobial agent, an antiseptic agent and a perfume.

20. The method according to item 11 or 12 above, wherein when the spraying composition is diluted with water to have a particulate cellulose concentration of 0.05% by weight, the resultant aqueous composition exhibits a transmittance of 80% or more to visible rays having a wavelength of 660 nm.

Hereinbelow, the present invention is described in detail.

Essentially, the present invention is concerned with a spray pack comprising a spray container device and, packed therein, the spraying composition. The spraying composition used in the present invention is obtained by dispersing particulate cellulose in a medium. More specifically, the spraying composition comprises a liquid dispersion medium (selected in accordance with the purpose of use of the composition (provided that the dispersion medium must not be a solvent for the cellulose)) and, dispersed therein, particulate cellulose as a viscosity modifier, wherein the composition may further comprise an additive selected in accordance with the purpose of use of the composition. Further, the present invention is also concerned with a method for forming a uniform, stable spray coating by using the above-mentioned spray pack.

The particulate cellulose used in the present invention is described below. First, a relatively simple explanation is made on the particulate cellulose, and next, a detailed explanation is made on the average degree of polymerization (DP) and average particle diameter of the cellulose used in the present invention, the fraction of the cellulose I type crystal component, and the fraction of the cellulose II type crystal component.

The spraying composition used in the present invention comprises particulate cellulose having an average degree of polymerization (DP) of not more than 300 and an average particle diameter of not more than 10 μm, and the composition has a cellulose content of from 0.1 to 5.0% by weight. In the present invention, the term "average degree of polymerization (DP)" means a weight average degree of polymerization, and the term "average particle diameter" means a volume average particle diameter.

The cellulose used in the present invention has an average degree of polymerization (DP) of from 10 to 300, preferably from 10 to 100, more preferably from 20 to 50. When the DP is more than 300, it is difficult to obtain a cellulose dispersion in which cellulose is dispersed as microparticles exhibiting a high degree of dispersion, thus leading to disadvantages in that the viscosity and dispersion stability of the spraying composition become low. When the DP is less than 10, most of the cellulose in the dispersion becomes water-soluble and hence cannot form microparticles which give high viscosity to the spraying composition used in the present invention, thus making it difficult for the cellulose to exhibit effects as a viscosity modifier.

The cellulose used in the present invention has an average particle diameter of not more than 10 μm, preferably not more than 2 μm, more preferably not more than 1 μm. The lower limit of the average particle diameter is 0.02 μm, which is close to the lower detection limit of the method used for measuring the average particle diameter in the present invention. When the cellulose has an average particle diameter of more than 10 μm, not only does it become difficult to obtain the high viscosity which is characteristic of the composition used in the present invention, but also the thixotropic properties of the composition are lowered.

Examples of celluloses satisfying such requirements include natural cellulose and particulate cellulose which is obtained by subjecting regenerated cellulose to an acid hydrolysis. It is preferred to use a commercially available microcrystalline cellulose and a mechanical pulverization product thereof, and it is also preferred to use particulate cellulose of low crystallinity obtained by using the below-mentioned method. However, with respect to the cellulose used in the present invention, there is no particular limitation as long as the cellulose meets the requirements mentioned above.

Hereinbelow, explanations are made on the methods for determining the average degree of polymerization (DP) and average particle diameter of the cellulose used in the present invention.

The average degree of polymerization (DP) of the cellulose is determined as follows. The cellulose is dispersed in a liquid dispersion medium (e.g., water) to obtain a cellulose dispersion. The cellulose dispersion is dried to obtain a dried cellulose sample. The dried cellulose sample is dissolved in cadoxene to obtain a diluted cellulose solution (cadoxene is a solution of a cadmium complex and has the following composition: $CdO/H_2NCH_2CH_2NH_2/NaOH/H_2O=5/28/1.4/165.6$ (weight ratio)). The specific viscosity of the diluted cellulose solution is measured (at 25° C.) using a Ubbelohde's viscometer. From the specific viscosity, an intrinsic viscosity value [η] is obtained. From the intrinsic viscosity value [η], a weight average degree of polymerization (DP) is obtained by calculation according to the following viscosity equation (1) and the conversion equation (2):

$$[\eta]=3.85\times10^{-2}\times M_w^{0.76} \tag{1}$$

$$DP=M_w/162 \tag{2}$$

(With respect to the method for determining the DP, reference can be made to W. Brown and R. Wikstroem, Euro. Polym. J., 1, (1965), pages 1–12.)

The average particle diameter of the cellulose is measured as follows. The cellulose is dispersed in a liquid dispersion medium (preferably, water) to obtain a cellulose dispersion. With respect to the obtained cellulose dispersion, measurement is performed at room temperature by means of a laser diffraction type particle size distribution measuring apparatus (Laser Diffraction/Scatting Type Particle Size Measuring Apparatus LA-920, manufactured and sold by HORIBA Ltd., Japan; the lower detection limit is 0.02 μm). For measuring the average particle diameter as in the state in which the association between the cellulose particles in the cellulose dispersion is broken as much as possible, a sample for measurement is prepared by the following procedure. The cellulose dispersion is diluted with water so that the cellulose content becomes about 0.5% by weight, to obtain a diluted cellulose dispersion. The diluted cellulose dispersion is subjected to a treatment for increasing the degree of dispersion, by means of a blender having a revolution rate of not less than 15,000 rpm, for 10 minutes to thereby obtain a sample for measurement of the average particle diameter of the cellulose. Subsequently, this sample is fed to the flow cell of the particle size distribution measuring apparatus and subjected to appropriate ultrasonic treatment. Then, the particle size distribution of the cellulose is measured (based on the particle volume distribution calculated by the Mie scattering theoretical formula). A volume average particle diameter is determined from the particle size distribution. The obtained volume average particle diameter is used as the average particle diameter of the cellulose.

It is preferred that the particulate cellulose used in the present invention has such a low crystallinity that the cellulose I type crystal component fraction ($x_I$) is 0.1 or less, more advantageously 0, and the cellulose II type crystal component fraction ($x_{II}$) is 0.4 or less, more advantageously 0.3 or less. The composition obtained using such particulate cellulose having low crystallinity exhibits high transparency. It is more preferred that such particulate cellulose having low crystallinity has an average particle diameter of 2 μm or less, more advantageously 1 μm or less. The composition obtained using such particulate cellulose exhibits not only higher transparency, but also viscosity increasing ability even at a relatively low cellulose content.

Hereinbelow, the methods for determining the fractions ($x_I$ and $x_{II}$) of cellulose I type and cellulose II type crystal components are described.

The fraction ($x_I$) of cellulose I type crystal component is obtained as follows. The cellulose is dispersed in a liquid dispersion medium to obtain a cellulose dispersion. The cellulose dispersion is dried to obtain a dried cellulose sample. The dried cellulose sample is pulverized into a powder, and the powder is subjected to tableting to obtain a tablet. The tablet is subjected to wide-angle X-ray diffractometry by the reflection method (using Rotaflex RU-300; manufactured and sold by Rigaku Corporation, Japan) (X ray source: CuKα). In the resultant wide-angle X-ray diffraction pattern (see FIG. 1), the absolute intensity $h_0$ of the peak (at $2\theta=15.0°$) ascribed to the (110) diffraction of the cellulose I type crystal, and the peak intensity $h_1$ corresponding to the distance between the top and base line of the same peak are determined. From the $h_0$ value and the $h_1$ value, the fraction ($x_I$) of cellulose I type crystal component is determined by the below-mentioned equation (3).

The fraction ($x_{II}$) of cellulose II type crystal component is obtained as follows. In the above-mentioned wide-angle X-ray diffraction pattern (see FIG. 1), the absolute intensity $h_0^*$ of the peak (at $2\theta=12.6°$) ascribed to the (110) diffraction of the cellulose II type crystal, and the peak intensity $h_1^*$ corresponding to the distance between the top and base line of the same peak are determined. From the $h_0^*$ value and the $h_1^*$ value, the fraction ($x_{II}$) of cellulose II type crystal component is determined by the below-mentioned equation (4).

$$x_I = h_1/h_0 \quad (3)$$

$$x_{II} = h_1^*/h_0^* \quad (4)$$

A diagram showing the method for determining $x_I$ and $x_{II}$ is shown in FIG. 1.

Next, an explanation is made on the liquid dispersion medium for dispersing the cellulose therein.

Usually, the liquid dispersion medium used in the present invention is water. However, a water-soluble organic solvent (e.g., an alcohol) may be used as a liquid dispersion medium. The water-soluble organic solvent may be used in addition to or instead of water. Further, a hydrophobic organic solvent may be used, depending on the purpose of use of the composition. These dispersion mediums may be used as a mixture thereof. In the present invention, the "liquid dispersion medium" is defined as a compound which is in liquid form at room temperature and under atmospheric pressure and which does not directly contribute to the functions of the composition used in the present invention. In the spraying composition used in the present invention, the liquid dispersion medium is used mainly for improving the dispersibility or dissolvability of the components of the composition.

When a water-soluble organic solvent is used as the dispersion medium, the amount of the organic solvent is from 1 to 90% by weight, preferably from 3 to 60% by weight, more preferably from 5 to 50% by weight, based on the weight of the composition. When the amount of the water-soluble organic solvent is less than 1% by weight, any appreciable effect cannot be obtained by the replacement of water with the water-soluble organic solvent. On the other hand, since the replacement of water which binds to the particulate cellulose is technically difficult, addition of the water-soluble organic solvent in an amount of more than 90% by weight is not recommendable.

Examples of water-soluble organic solvents include alkyl alcohols having 1 to 4 carbon atoms, such as methanol, ethanol, n-propyl alcohol, iso-propyl alcohol, n-butyl alcohol, sec-butyl alcohol, tert-butyl alcohol, and the like; ketones or keto alcohols, such as dimethylformamide, dimethylacetamide, acetone, diacetone alcohol, and the like; ethers, such as tetrahydrofuran, dioxane, and the like; alkylene glycols having an alkylene group having 2 to 6 carbon atoms, such as ethylene glycol, propylene glycol, butylene glycol, triethylene glycol, 1,2,6-hexane triol, thiodiglycol, hexylene glycol, diethylene glycol, and the like; cellosolves, such as ethylene glycol monomethyl ether, ethylene glycol monoethyl ether, and the like; Carbitols, such as diethylene glycol monomethyl ether, diethylene glycol monoethyl ether, ethylene glycol mono-n-butyl ether, diethylene glycol-n-butyl ether, triethylene glycol-n-butyl ether, and the like; 1,2-alkyldiols, such as 1,2-hexanediol, 1,2-octanediol, and the like; polyethylene glycol; polypropylene glycol; glycerol and derivatives thereof; N-methyl-2-pyrrolidone; 2-pyrrolidone; and 1,3-dimethyl-2-imidazolidinone. However, examples of water-soluble organic solvents are not limited to those which are mentioned above. In the present invention, the "water-soluble organic solvent" is defined as an organic solvent which exhibits a solubility in water (even if the solubility is small) and which is used at a concentration (or in an amount) which is not more than the solubility of the organic solvent in water.

When a mixture of water and a water-soluble organic solvent, or an emulsion comprising water and a hydrophobic organic solvent, is used as the liquid dispersion medium, advantages can be obtained not only in that various types of functional additives can be dissolved or dispersed in the liquid dispersion medium, but also in that the drying rate of the liquid dispersion medium (after spraying) can be adjusted easily, as compared to the case of use of water only.

When a mixture of water and a water-soluble organic solvent is used as the liquid dispersion medium, the weight ratio of water-soluble organic solvent/water is from 0.01 to 9, preferably from 0.03 to 2. When the weight ratio is less than 0.01, any appreciable effect cannot be obtained by the replacement of water with a water-soluble organic solvent. On the other hand, since the replacement of water which binds to the particulate cellulose is technically difficult, use of the water-soluble organic solvent in a weight ratio (water-soluble organic solvent/water) of more than 9 is not recommendable.

Further, when an emulsion comprising water and a hydrophobic organic solvent is used as the liquid dispersion medium, the weight ratio of hydrophobic organic solvent/water is from 0.01 to 2, preferably from 0.03 to 1. When the weight ratio is less than 0.01, any appreciable effect cannot be obtained by the replacement of water with a hydrophobic organic solvent. When the weight ratio is more than 2, use of a large amount of surfactant is necessary for obtaining a stable emulsion, thus causing a disadvantage in that the formulation of the spraying composition is greatly limited.

Among the above-mentioned water-soluble organic solvents, it is preferred to use a water-soluble alcohol (such as ethanol or ethylene glycol), that is, it is preferred to use an aqueous solution of a water-soluble alcohol as the liquid dispersion medium, since the use of such liquid dispersion medium makes it possible to obtain a spraying composition having high transparency over a relatively broad range of formulation of the components. In the present invention, the "water-soluble alcohol" is defined as an alcohol which exhibits a solubility in water (even if the solubility is small) and which is used at a concentration (or in an amount) which is not more than the solubility of the alcohol in water.

Examples of hydrophobic organic solvents include aliphatic hydrocarbons or derivatives thereof, such as n-pentane, n-hexane, n-heptane, 1-butene, 1-pentene, and the like; benzene or derivatives thereof; toluene or derivatives thereof; aromatic hydrocarbons, such as xylene, decalin, and the like; esters, such as ethyl acetate, propyl lactate, propyl butyrate, and the like; and ethers, such as methyl butyl ether and the like. However, the hydrophobic organic solvent is not limited to these examples. When a water-insoluble hydrophobic organic solvent is used as the liquid dispersion medium, the solvent may be emulsified by effecting an appropriate emulsifying treatment, depending on the purpose of use of the spraying composition. Further, a solvent (such as a water-soluble alcohol) which is soluble in both water and a water-insoluble hydrophobic organic solvent, may be added to water and the water-insoluble hydrophobic organic solvent to thereby form a homogeneous, mixed solvent comprising three or more solvents.

The composition used in the present invention comprises the above-mentioned particulate cellulose and the above-mentioned liquid dispersion medium. With respect to the ratio between these components of the composition, an explanation is made below.

The cellulose content required for the composition used in the present invention having an appropriately high viscosity varies depending on the properties (DP, the average particle diameter and the crystal component fraction) of the cellulose. However, the cellulose content of the composition is generally from 0.1 to 5.0% by weight, preferably from 0.3 to 4.0% by weight, more preferably from 0.5 to 2.5% by weight. When the cellulose content of the composition is less than 0.1% by weight, it is likely that the excellent anti-dripping properties (after spraying) aimed at by the present invention cannot be obtained. On the other hand, when the cellulose content of the composition is more than 5.0% by weight, the viscosity of the composition becomes extremely high, leading to a problem in that, when the composition is packed in a spray container, the composition is likely to contain air, making it difficult to perform a stable spraying.

Figure 2:
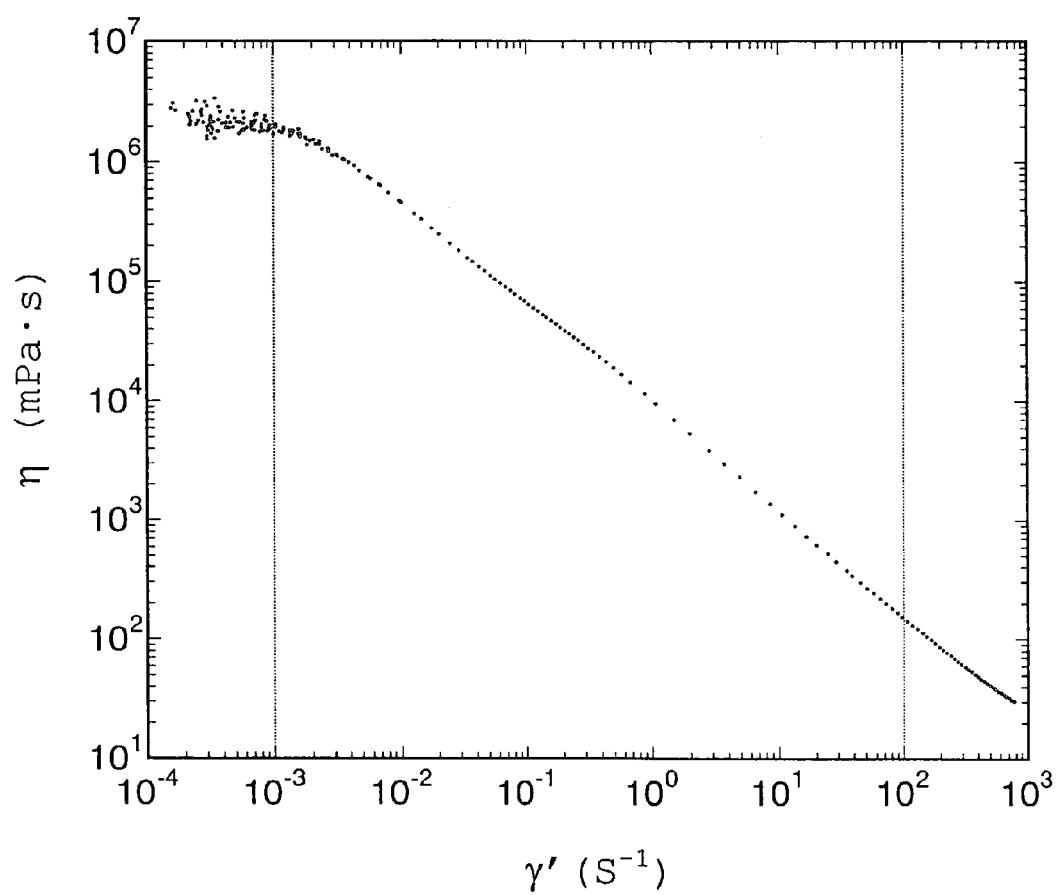
FIG. 2 is a graph showing the viscosity-shear rate curve obtained with respect to a cellulose/water dispersion (used in the present invention) having a cellulose content of 1.5% by weight (sample S3), wherein the measurement for obtaining the curve was performed using a cone-plate type rotating viscometer at 25° C.
Figure 3:
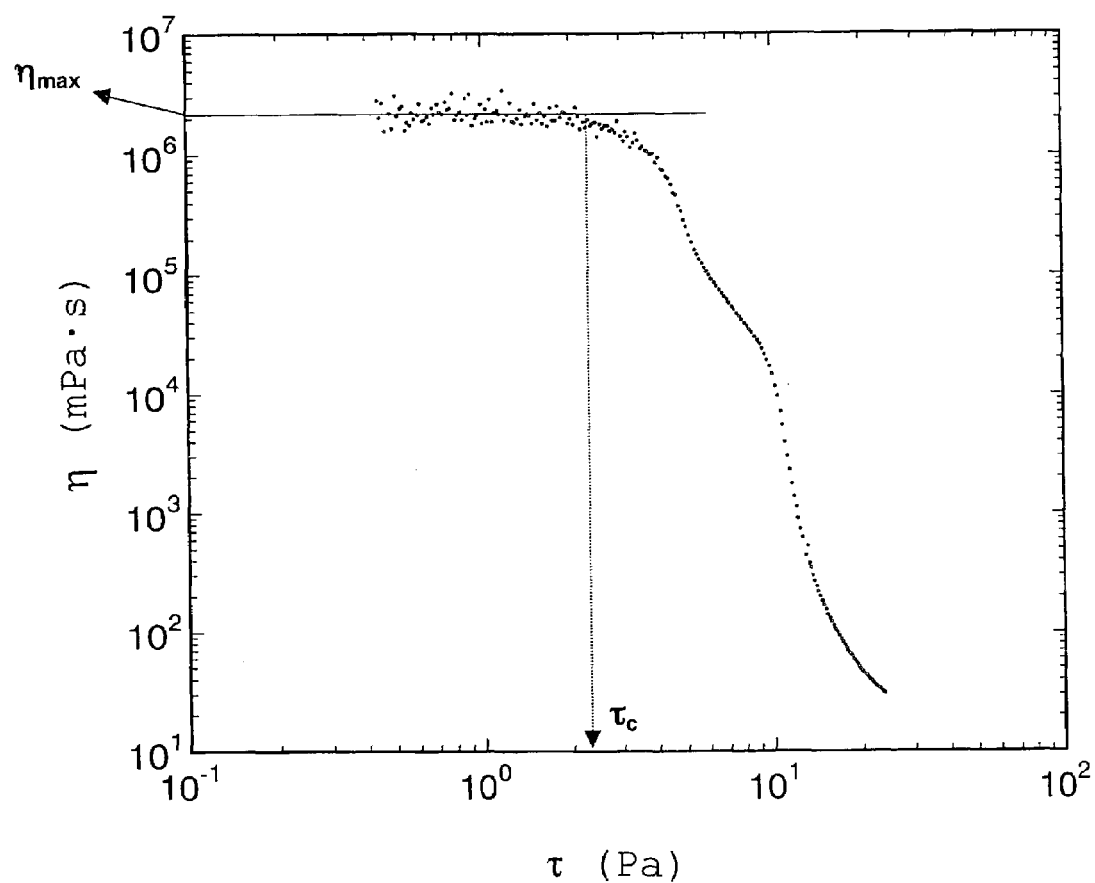
FIG. 3 is a graph showing the method for determining a maximum viscosity value ($\eta_{max}$) in the viscosity-shear stress curve obtained with respect to a cellulose/water dispersion (used in the present invention) having a cellulose content of 1.5% by weight (sample S3), wherein the measurement for obtaining the curve was performed using a cone-plate type rotating viscometer at 25° C.

It is required that the composition used in the present invention exhibit a maximum viscosity value ($\eta_{max}$) of $1 \times 10^3$ mPa·s or more in the viscosity-shear stress curve obtained, with respect to the composition, using a cone-plate type rotating viscometer in a shear rate region of from $1 \times 10^{-3}$ s$^{-1}$ to $1 \times 10^2$ s$^{-1}$ and at 25° C. In FIGS. 2 and 3, as specific examples of measurement data, there are, respectively, shown a viscosity ($\eta$)-shear rate ($\gamma$, i.e., gamma dot) curve and a viscosity ($\eta$)-shear stress ($\pi$) curve which were obtained by measurement performed at 25° C. with respect to a cellulose/water dispersion (used in the present invention) having a cellulose content of 1.5% by weight (sample S3).

As a cone-plate type rotating viscometer, RS-100, manufactured and sold by Haake, Germany, was used (wherein, in the cone-plate, the cone angle was 4° and the diameter of the plate was 35 mm). In FIG. 3, when the $\pi$ value is about 2 Pa or less, the $\eta$ value (viscosity) is almost constant and does not depend on the $\pi$ value, that is, the so-called Newtonian viscosity is exhibited; however, when the $\pi$ value is more than 2 Pa, the $\eta$ value (viscosity) is sharply decreased. For example, when the $\pi$ value=20 Pa, the $\eta$ value (viscosity) is as low as only 50 mPa·s. This data shows the high thixotropy of the composition used in the present invention. In addition, it should be noted that the data of FIG. 3 also shows that the critical shear stress value ($\pi_c$ in FIG. 3) (at which the viscosity ($\eta$) exhibits a sharp decrease) is extremely low, as compared to the case of the viscosity ($\eta$)-shear stress ($\pi$) curves which are obtained, with respect to conventional materials. That is, the composition used in the present invention has an advantage in that, irrespective of its extremely high viscosity, the composition exhibits a low viscosity when only a low shear stress is applied to the composition. By virtue of this property, the composition used in the present invention can be drawn up by suction to the spray nozzle through the suction tube. The data of FIG. 3 shows that sample S3 (exhibiting a maximum viscosity value ($\eta_{max}$) of $2 \times 10^6$ mPa·s) exhibits a critical shear stress value ($\pi_c$) of 2.2 Pa (wherein sample S3 was produced in an Example of the present specification). This data of FIG. 3 should be compared, for example, with the data of sample H2 (general purpose gel), which was used in a Comparative Example of the present specification. Sample H2 is a 0.5% by weight aqueous solution of Carbopol 940™ and exhibits a maximum viscosity value ($\eta_{max}$) of $3 \times 10^6$ mPa·s. Although the $\eta_{max}$ value ($3 \times 10^6$ mPa·s) of Sample H2 is at the same level as that of sample S3, sample H2 exhibits a critical shear stress value ($\pi_c$) as high as 26 Pa, which is extremely high, as compared to the $\pi_c$ value (2.2 Pa) of sample S3.

When the composition exhibits a maximum viscosity value ($\eta_{max}$) of less than $1 \times 10^3$ mPa·s, the viscosity is too low, so that it is likely that the excellent anti-dripping properties (after spraying) aimed at by the present invention cannot be obtained. In cases where the spraying is performed so that the coating density becomes relatively low, satisfactory anti-dripping properties (after spraying) can be obtained when the requirement that the $\eta_{max}$ value $\geq 1 \times 10^3$ mPa·s is satisfied. However, in cases where the spraying is performed so that the coating density becomes relatively high, it is possible that satisfactory anti-dripping properties (after spraying) cannot be obtained even when the requirement that the $\eta_{max}$ value $\geq 1 \times 10^3$ mPa·s is satisfied. For ensuring that the effects of the present invention (such as excellent anti-dripping properties (after spraying)) can be obtained irrespective of the spraying conditions used, it is preferred that the $\eta_{max}$ value $\geq 5 \times 10^5$ mPa·s, and it is more preferred that the $\eta_{max}$ value $\geq 2 \times 10^6$ mPa·s. The viscosity of the spraying composition may be adjusted depending on the purpose of use of the spraying composition. In many cases, when the $\eta_{max}$ value $\geq 5 \times 10^5$ mPa·s, the composition used in the present invention becomes a gel and exhibits no fluidity. From the viewpoint of stable spraying, it is desired that the $\eta_{max}$ value is not more than $1 \times 10^9$ mPa·s.

The composition used in the present invention may contain at least one functional additive in accordance with the purpose of use of the composition. In the present invention, the term "functional additive" is used as a generic name for compounds which can have any contribution to the purpose of use of the spraying composition in the present invention. Representative examples of functional additives include an oil compound, a humectant, a surfactant, a metal oxide, an ultraviolet screener, an inorganic salt, a metal powder, a gum, a dye, a pigment, a silica compound, a latex, a water-soluble polymer, an amino acid, a cosmetic ingredient, a pharmaceutical, an insecticide, a deodorizer, an anti-microbial agent, an antiseptic agent and a perfume. These are used individually or in combination. It is important that the composition containing the functional additive be homogeneous and that the functional additive does not spoil the effects of the spraying composition used in the present invention.

For example, in the case where water is used as the liquid dispersion medium of the composition used in the present invention, when an oil compound (such as liquid paraffin) is used as a cosmetic coating oil (functional additive), the cellulose content is chosen so that a homogeneous O/W emulsion is formed. For example, when liquid paraffin and water are used in a (liquid paraffin/water) weight ratio of 20/80 (g/g) and the composition is prepared by a method in which the emulsification is performed using an ordinary homomixer, it is desired that the cellulose content is from 0.8 to 2.5% by weight. Needless to say, these requirements with respect to the formulation of the spraying composition may vary depending on the type of the oil compound and the ratios of the components of the spraying composition.

When a metal powder, such as a metal oxide powder (e.g., titanium oxide powder) or a copper powder, is used as a functional additive, it is necessary that the combination of the dispersion medium and the functional additive is chosen so that the solid microparticles (metal powder) do not exhibit precipitation or aggregation, thereby achieving uniform dispersion of the solid microparticles.

Hereinafter, specific examples of functional additives which may be incorporated in the composition used in the present invention are described.

Examples of oil compounds include animal fats and oils and vegetable fats and oils, such as jojoba oil, macadamia nut oil, avocado oil, evening primrose oil, mink oil, rapeseed oil, castor oil, sunflower oil, corn oil, cacao oil, coconut oil, rice bran oil, olive oil, almond oil, sesame oil, safflower oil, soybean oil, camellia oil, persic oil, cotton seed oil, vegetable wax, palm oil, palm kernel oil, egg yolk oil, lanolin, and squalene; hydrocarbons, such as synthetic triglyceride, squalane, liquid paraffin, vaseline, ceresin, microcrystalline wax, and isoparaffin; waxes, such as carnauba wax, paraffin wax, spermaceti, beeswax, candelilla wax, and lanolin; higher alcohols, such as cetanol, stearyl alcohol, lauryl alcohol, cetostearyl alcohol, oleyl alcohol, behenyl alcohol, lanolin alcohol, hydrogenated lanolin alcohol, hexyldecanol, and octyldodecanol; higher fatty acids, such as lauric acid, myristic acid, palmitic acid, stearic acid, behenic acid, isostearic acid, oleic acid, linolenic acid, linoleic acid, oxystearic acid, undecylenic acid, lanolin fatty acid, hard lanolin fatty acid, and soft lanolin fatty acid; cholesterols and derivatives thereof, such as cholesteryl-octyldodecyl-behenyl; esters, such as isopropyl myristate, isopropyl palmitate, isopropyl stearate, glycerol 2-ethylhexanoate, and butyl stearate; polar oils, such as diethylene glycol monopropyl ether, polyoxyethylene polyoxypropylene pentaerythritol ether, polyoxypropylene butyl ether, and ethyl linoleate; silicones and derivatives thereof, such as amino-modified silicone, epoxy-modified silicone, carboxyl-modified silicone, carbinol-modified silicone, methacryl-modified-silicone, mercapto-modified silicone, phenol-modified silicone, silicone having a terminal reactive group, silicone which is modified with hetero-functional groups, polyether-modified silicone, methylstyryl-modified silicone, alkyl-modified silicone, higher fatty acid ester-modified silicone, hydrophilic group-modified silicone, higher alkoxy-modified silicone, higher fatty acid-containing silicone, and fluorine-modified silicone; more specifically, silicone resin, methyl phenyl polysiloxane, methyl polysiloxane, octamethylcyclotetrasiloxane, decamethylcyclopentasiloxane, dodecamethylcyclohexane siloxane, methylcyclopolysiloxane, octamethyltrisiloxane, decamethyltetrasiloxane, polyoxyethylene/methylpolysiloxane copolymer, polyoxypropylene/methylpolysiloxane copolymer, poly(oxyethylene/oxypropylene)methylpolysiloxane copolymer, methylhydrogenpolysiloxane, tetrahydrotetramethyl-cyclotetrasiloxane, stearoxymethylpolysiloxane, cetoxy-methylpolysiloxane, methylpolysiloxane emulsion, highly polymeric methylpolysiloxane, trimethylsiloxy silic acid, crosslinkable methylpolysiloxane, and crosslinkable methylphenylpolysiloxane. The oil compound is not limited to these examples.

Examples of humectants include polyhydric alcohols, such as maltitol, sorbitol, glycerin, propylene glycol, 1,3-butylene glycol, polyethylene glycol, and glycol; organic acids and salts thereof, such as sodium pyrrolidonecarboxylate, sodium lactate, and sodium citrate; hyaluronic acid and salts thereof, such as, sodium hyaluronate; hydrolysates of yeast and of yeast extract; fermentation metabolites, such as a yeast culture broth and a culture broth of lactic acid bacteria; water-soluble proteins, such as collagen, elastin, keratin, and sericin; peptides and salts thereof, such as collagen hydrolysate, casein hydrolysate, silk hydrolysate, and sodium polyaspartate; saccharides, polysaccharides and derivatives thereof, such as trehalose, xylobiose, maltose, sucrose, glucose and plant-derived mucilaginous polysaccharides; glycosaminoglycans and salts thereof, such as water-soluble chitin, chitosan, pectin, and chondroitin sulfate and salts thereof; amino acids, such as glycine, serine, threonine, alanine, aspartic acid, tyrosine, valine, leucine, arginine, glutamine, and proline; betaines, such as N-trimethylglycine; sugar amino acid compounds, such as aminocarbonylation products; plant extracts, such as extracts of aloe and horse chestnut; and nucleic acid-related substances, such as urea, uric acid, ammonia, lecithin, lanolin, squalane, squalene, glucosamine, creatinine, DNA, and RNA. The humectant is not limited to these examples.

Examples of surfactants include nonionic surfactants, such as propylene glycol fatty acid ester, glycerol fatty acid ester, polyoxyethylene glycerol fatty acid ester, polyglycerol fatty acid ester, sorbitan fatty acid ester, polyoxyethylene sorbitan fatty acid ester, polyoxyethylene sorbitol fatty acid ester, polyethylene glycol fatty acid ester, polyoxyethylene castor oil, polyoxyethylene hydrogenated castor oil, polyoxyethylene alkyl ether, polyoxyethylene phytosterol, polyoxyethylene polyoxypropylene alkyl ether, polyoxyethylene alkyl phenyl ether, polyoxyethylene lanolin, polyoxyethylene lanolin alcohol, polyoxyethylene beeswax derivatives, polyoxyethylene alkyl amine, polyoxyethylene fatty acid amide, polyoxyethylene alkyl phenyl formaldehyde condensate, and polyoxyethylene alkyl ether phosphoric acid (phosphate); anionic surfactants, such as alkylsulfuric ester, polyoxyethylene alkyl sulfuric ester, alkylbenzenesulfonate, and α-olefin sulfonate; cationic surfactants, such as alkyltrimethylammonium chloride, dialkyldimethylammonium chloride, and benzalkonium chloride; amphoion surfactants, such as alkyldimethylaminoacetobetaine and alkylamidodimethylaminoacetobetaine; natural substances having surface activity, such as lecithin, lanolin, cholesterol, and saponin; and hypoallergenic surfactants, such as sulfosuccinates and ethylene oxide/propylene oxide block copolymers. The surfactant is not limited to these examples.

Examples of metal oxides include titanium dioxide, alumina, zinc dioxide, colcothar, yellow oxide, and black iron oxide. The metal oxide is not limited to these examples. From the viewpoint of achieving good spraying properties of the composition, it is preferred that the metal oxide is in such a microparticulate form that it has an average particle diameter of 10 μm or less, preferably 5 μm or less.

Examples of ultraviolet screeners include paraaminobenzoic acid and derivatives thereof; methyl-7N-acetylallantoilanylate; butylmethoxybenzoylmethane; paramethoxycinnamic acid derivatives, such as di-paramethoxycinnamic acid-mono-2-glyceryl ethyl hexanoante, and octylcinnamate; salicylic acid derivatives, such as amyl salicylate; benzophenone derivatives, such as 2,4-dihydroxybenzophenone; dimethoxybenzylidenedioxo-imidazoline ethylhexylpropionate; acetylated lanolin alcohol (liquid state); scutellaria root (i.e., oughon) extract; and trianilino-p-carboethylhexyloxytriazine. The ultraviolet screener is not limited to these examples.

With respect to the inorganic salt, there is no limitation, and there can be used any inorganic salt which is soluble in the liquid dispersion medium. Examples of inorganic salts include sodium chloride, calcium chloride, magnesium chloride, ammonium sulfate, and calcium phosphate. However, depending on the amount of an inorganic salt used, it is possible that the inorganic salt causes strong aggregation of cellulose. Therefore, the amount of an inorganic salt is adjusted so as not to cause adverse effects on the spraying properties of the composition.

With respect to the metal powder, there is no limitation, and there can be used a powder of any metal, such as gold, silver, copper, aluminum, magnesium, zinc and iron. However, from the viewpoint of achieving good spraying properties of the composition, it is preferred that the metal powder has an average particle diameter of 10 μm or less, preferably 5 μm or less.

Examples of gums include gum arabic, xanthan gum, guar gum, locust bean gum, quince seed, and carrageenan. The gum is not limited to these examples.

The dye and pigment can be appropriately selected from those employed in the various fields, such as fiber coloring, various types of printing, copying machines, and writing instruments. The dye and pigment are not limited to those employed in these fields. There can be used any dye and/or any pigment as long as they have a coloring ability.

Examples of silica compounds include zeolite, montmorillonite, asbestos, smectite, mica, fumed silica, colloidal silica, and nanoporous silica. The silica compound is not limited those examples. From the view-point of achieving good spraying properties of the composition, it is preferred that the silica compound is in such a microparticulate form that it has an average particle diameter of 10 μm or less, preferably 5 μm or less.

Examples of latexes include a styrene-butadiene copolymer latex and an acrylic polymer latex. There can be used any polymer latex which is obtained by an emulsion polymerization.

Examples of water-soluble polymers include polyethylene glycol, polyvinyl alcohol, cationized cellulose, carboxyvinyl polymer, polyvinyl pyrrolidone, a polyvinyl pyrrolidone/vinyl acetate copolymer, polyacrylic acid, polyacrylamide, alginic acid, polydextrose, carboxymethyl cellulose, and hydroxyethyl cellulose. The water-soluble polymer is not limited to these examples.

With respect to the amino acid, any known amino acid (such as glutamic acid, aspartic acid, glycine and lysine) can be used.

Examples of cosmetic ingredients include arbutin, kojic acid, ascorbic acid and derivatives thereof, such as magnesium-L-ascorbyl-2-phosphate, glutathione, glycyrrhiza extract, clove extract, tea extract, astaxanthin, bovine placenta extract, tocopherol and derivatives thereof, tranexamic acid and salts thereof, azulene, whitening elements, such as γ-hydroxybutyric acid; organic acids, such as citric acid, malic acid, tartaric acid, lactic acid, adipic acid, glutamic acid, aspartic acid, and maleic acid; B vitamins, such as vitamin B6 hydrochloride, vitamin B6 tripalmitate, vitamin B6 dioctanoate, and vitamin B2 and derivatives thereof; C vitamins, such as ascorbic acid, ascorbic acid sulfate, and ascorbic acid phosphate; E vitamins, such as α-tocopherol, β-tocopherol, and γ-tocopherol; D vitamins; other vitamins, such as vitamin H and pantothenic acid; blood circulation stimulators, such as nicotinic acid amide, benzyl nicotinate, γ-oryzanol, allantoin, glycyrrhizic acid (salt), glycyrrhetic acid and derivatives thereof, hinokitiol, bisabolol, eucalyptol, thymol, inositol, saponins, (e.g., quillaia saponin, azuki-bean saponin and sponge gourd saponin), tranexamic acid, pantothenylethyl ether, ethynylestradiol, placenta extract, sialid extract, cepharanthine, and vitamin E and derivatives thereof; local stimulators, such as capsicum tincture, ginger tincture, cantharis tincture, and benzyl nicotinate; anti-inflammatory agents, such as glycyrrhetic acid, glycyrrhizic acid derivatives, allantoin, azulene, aminocaproic acid, and hydrocortisone; astringents, such as zinc oxide, zinc sulfate, allantoin hydroxyaluminum, aluminum chloride, zinc sulfophenolate, and tannic acid; algefacients (refreshing agents), such as menthol and camphor; antihistamine agents; silicon-containing compounds, such as polymeric silicone and cyclic silicone; various pharmaceuticals, such as antioxidants, e.g., tocopherols and gallic acid; and extracts of natural products, such as plants, animals, bacteria and a part of a natural product, wherein the extracts are obtained by extraction using a solvent (such as, an organic solvent, an alcohol, a polyhydric alcohol, water, or a water-soluble alcohol) or by hydrolysis. Examples of such natural products include yeast (such as, saccharomyces), filamentous fungi, bacteria, bovine placenta, human placenta, human umbilical cord, wheat grains, soybeans, bovine blood, swine blood, cockscomb, chamomile, cucumber, rice, shea butter, white birch, tea, tomato, garlic, witch hazel (i.e., hamamelis), rose, sponge gourd, hop, peach, apricot, lemon, kiwi fruit, dokudami (i.e., *Hottuynia cordata*), capsicum, *Sophora flavescens*, sorrel, nuphar rhizome (i.e., spatterdock), sage, yarrow, mallow, cnidium rhizome, sialid, thyme, Japanese angelica root, spruce, birch, field horsetail, horse chestnut tree, strawberry geranium, arnica, lily, mugwort, peony, aloe, aloe vera, scutellaria root (i.e., oughon), cork tree, silk tree, safflower, gardenia fruit, lithospermum root, jujube fruit, dried orange peel, ginseng, coix seed, adlay, gardenia, and sawara cypress. The cosmetic ingredient is not limited to those examples.

With respect to the pharmaceutical, there is no limitation, and there can be used any pharmaceutical (inclusive of traditional Chinese medicines) which exhibits a medicinal effect. However, the efficacy of a pharmaceutical greatly varies depending on a compound which coexists with the pharmaceutical. Therefore, the formulation of the composition should be appropriately chosen so that the pharmaceutical can exhibit a satisfactory efficacy.

Representative examples of insecticides include camphor, naphthalene, paradichlorobenzene, paraformaldehyde, chloropicrin, pyrethrum, sulfonbenzaldehyde, and a phenylmethane compound. The insecticide is not limited to these examples.

With respect to the deodorizer, there is no limitation, and there can be used any compound which exhibits a deodorizing effect. The deodorizer may or may not be solid and may or may not be dissolvable. When the deodorizer is solid, from the viewpoint of achieving good spraying properties of the composition, it is preferred that the deodorizer is in such a microparticulate form as have an average particle diameter of 10 μm or less, preferably 5 μm or less.

Examples of antimicrobial agents and antiseptic agents include benzoic acid and salts thereof, salicylic acid and salts thereof, sorbic acid and salts thereof, alkyl parahydroxybenzoate (e.g., ethylparaben or butylparaben) and salts thereof, dehydroacetic acid and salts thereof, parachlorometacresol, hexachlorophene, boric acid, resorcin, tribromosalan, orthophenylphenol, chlorhexidine gluconate, thiram, photosensitizing dye No. 201, phenoxyethanol, benzalkonium chloride, benzethonium chloride, halocarban, chlorhexidine chloride, trichlorocarbanilide, tocopherol acetate, zinc pyrithione, hi-nokitiol, phenol, isopropyl methylphenol, 2,4,4-trichloro-2-hydroxyphenol, and hexachlorophene. The antimicrobial agent and antiseptic agent are not limited to these examples.

With respect to the perfume, there is no limitation, and there can be used any material which serves as a perfume. It is preferred that the formulation of the composition is appropriately chosen so that the adverse effects, if any, of other components on the scent of the perfume are as small as possible.

With respect to the ionic compound as a functional additive, an explanation is made below. It is preferred that, in the composition, the content of the functional additive other than the ionic compound is from 0.1 to 60% by weight, more advantageously from 0.1 to 40% by weight, still more advantageously from 0.2 to 30% by weight.

The functional additive is not limited to these. Any other functional additives which are appropriately selected may be incorporated into the composition, depending on the purpose of use of the composition. The functional additives are used individually or in combination. In selecting a functional additive, it is especially important that the composition containing the functional additive selected have a good homogeneity such that no grainy feeling or no phase separation is exhibited. Also, it is especially important that the composition containing the functional additive selected exhibit almost no stringiness.

The spraying composition used in the present invention is a microparticle dispersion. In this respect, the composition used in the present invention is a colloid. However, the composition used in the present invention has a unique property that it can form a transparent, highly stable gel. This means that the spraying composition used in the present invention is a very unique colloid which has conventionally not been reported. The reason for the presence of such unique property of the spraying composition used in the present invention resides in that particulate cellulose (which is the main component) has the high ability to form hydrogen bonds therebetween. As only other transparent gels having a similar property, there can be mentioned an aqueous dispersion of fumed silica and an aqueous dispersion of hydrophilic smectite. However, these conventional dispersions pose problems in that, when an organic solvent is added, aggregation is likely to occur and that the coating forming abilities of these dispersions are extremely poor. Therefore, with respect to the practical usefulness, the composition used in the present invention is distinct from these conventional dispersions. It is known that, in general, when an ionic compound is added to a colloidal dispersion, the colloidal dispersion undergoes aggregation. Specifically, in the case of a certain type of colloidal dispersion, when an ionic compound, such as an inorganic salt having the strong ability to induce aggregation (e.g., a trivalent inorganic salt, such as ammonium chloride), is added to the dispersion, aggregation occurs even when the amount of the ionic compound is as small as only 0.1% by weight, thus adversely affecting the stability or the like of the resultant composition. By contrast, the present inventors have found that, when an ionic compound as a functional additive is added to the composition used in the present invention under specific conditions, a stable composition can be provided.

That is, the present inventors have found the following. When a functional additive is added to the spraying composition used in the present invention, the stability of the resultant additive-containing composition may vary depending on the type of the additive used, the type of the dispersion medium used, the cellulose content and the like. However, even in the case of the use of an ionic compound as a functional additive, when the content of the ionic compound (as a functional additive) in the composition is from 0.1 to 10% by weight, the composition can maintain a high stability. The content of the ionic compound in the composition is preferably in the range of from 0.1 to 5% by weight, more preferably from 0.2 to 3% by weight. When the content of the ionic compound is less than 0.1% by weight, the ionic compound is generally incapable of performing a satisfactory function as a functional additive. On the other hand, when the content of the ionic compound is more than 10% by weight, the stability of the composition becomes lowered.

In the present invention, the term "ionic compound" is used as a generic name for compounds which are capable of being dissolved as an ion in the dispersion medium. Examples of ionic compounds include amphoteric compounds, cationic compounds and anionic compounds. The cellulose, optional functional microparticles and the like which are contained in the composition used in the present invention may induce colloidal properties in the composition. Therefore, when the ionic compound is added to the composition, the formulation of the composition is adjusted so that the content of the ionic compound is in the above-mentioned range and that the stability of the components of the composition is maintained at a high level (this means a state in which, when the composition is visually observed, the composition is homogeneous and exhibits no phase separation of the components with the lapse of time).

The type of the ionic compound is especially important for choosing the formulation of the composition. Use of an amphoteric compound or a cationic compound is especially preferred because these ionic compounds can be widely used with only a relatively small limitation as long as the amount of the ionic compound is in the above-mentioned range.

The term "amphoteric compound" used herein means a compound which has both a positive ionic group and a negative ionic group in one molecule and which is electrically neutral in such a state as dissolved in the dispersion medium. Examples of amphoteric compounds include various amino acids and salts thereof and betaines. Examples of cationic compounds include cationic surfactants (such as alkyltrimethylammonium chloride and dialkyldimethylammonium chloride), water-soluble cationic polymers (such as cationized cellulose) and low molecular weight cationic molecules, such as lysine and lysine salts. Examples of anionic compounds include anionic surfactants (such as alkyl sulfate esters and polyoxyethylene alkyl sulfate esters), water-soluble anionic polymers (such as polyacrylic acid and carboxymethyl cellulose), and water-soluble low molecular weight organic compounds, such as glutamic acid, a glutamate, citric acid and a citrate, which are functional additives capable of functioning as an anion or existing in the form of an anion in the composition. Further examples of ionic compounds include inorganic salts which are soluble in the dispersion medium, such as sodium chloride, magnesium chloride, calcium chloride, sodium hydrogencarbonate, sodium carbonate, ammonium sulfate, potassium phosphate and ammonium nitrate. There can also be mentioned inorganic acids, such as sulfuric acid, hydrochloric acid and phosphoric acid, and other inorganic compounds, such as sodium hydroxide and potassium hydroxide.

Stringing is a phenomenon which is caused by the presence of a high molecular weight polymer component dissolved in the liquid dispersion medium. Therefore, for example, when a water-soluble polymer is dissolved in the aqueous dispersion medium, the molecular weight and amount of the polymer should be appropriately selected so as to prevent the occurrence of stringing.

The spraying composition used in the present invention has high thixotropy and, thus, when this composition is sprayed, the viscosity of the composition is lowered to thereby form an excellent spray or foam, but the original viscosity of the composition is quickly recovered before the sprayed fine particles of the composition attach to a surface to be coated. Therefore, dripping is very unlikely to occur after the sprayed composition attaches to a surface to be coated. Further, the spraying composition used in the present invention exhibits the following excellent properties. The composition exhibits an excellent thermal stability such that the viscosity of the composition is not lowered even at a high temperature of 50° C. or more. The composition is free from tackiness which is characteristic of a water-soluble polymer. The composition exhibits excellent spreadability after coating. The composition exhibits high dispersion stability and is capable of forming a strong coating, thereby enabling the formation of a strong coating having immobilized thereon a functional compound. At the same time, with respect to the fixation of the fine particles of the sprayed composition to the surface coated, such as skin and a substrate, the spraying composition used in the present invention is largely improved by virtue of the amphiphilic properties and viscosity increasing effects of cellulose, as compared to the case of the liquid dispersion medium used solely.

In addition, since cellulose (having a high safety) is used as a viscosity modifier for the spraying composition used in the present invention, the composition is advantageous in that, when components having a high safety are selected as the additional components for the composition, it is easy to design the formulation of the composition so as to, for example, minimize the occurrence of irritation even after the drying of the liquid dispersion medium of the composition which has been applied to the human body (such as skin). That is, it is possible to provide a spraying composition having a very high safety.

Further, the composition used in the present invention can be produced so as to have high transparency, when an appropriate type of cellulose and an appropriate formulation are selected. Herein, the term "high transparency" means that, when the composition is diluted with water to have a particulate cellulose concentration of 0.05% by weight, the resultant aqueous composition exhibits a transmittance of 80% or more, preferably 90% or more, to visible rays having a wavelength of 660 nm.

Further, the composition of the present invention

When the composition which is produced so as to have high transparency is sprayed, the resultant spray coating layer maintains its transparency even after drying. Therefore, such a spraying composition can be used advantageously in fields where high transparency and high smoothness are required for the spray coating layer. For preparing a composition which can form a spray coating layer having a satisfactory level of transparency and smoothness, it is important to prevent not only cellulose but also components other than cellulose from undergoing aggregation. This is because the transparency of the composition is markedly lowered by aggregation. Further, for the purpose of obtaining high transparency, it is necessary to limit the content of the ionic compound to a value within the above-mentioned range.

For example, for adding a surfactant to the composition without lowering the transparency thereof, it is effective to add a nonionic surfactant or an amphoteric surfactant, such as betaine.

Further, as mentioned above, when a water-soluble polymer is added as a dispersion stabilizer for the dispersed components (such as a pigment), it is important that the polymer be added in a limited amount which does not cause stringing, thereby maintaining the spraying properties of the composition. From the viewpoint of improving the transparency of the composition, polymeric electrolytes (ionic compounds), such as polyacrylic acid, alginic acid and carboxymethyl cellulose, are disadvantageous because they tend to promote the aggregation of cellulose and lower the transparency of the spraying composition. Therefore, it is desired that the amount of the polymeric electrolyte is lowered to a level which causes no adverse effects on the transparency of the spraying composition. Alternatively, it is desired that a nonionic compound, such as polyethylene glycol or polyvinyl alcohol, or a mixture of a nonionic water-soluble polymer and a polymeric electrolyte is used as a dispersion stabilizer.

With respect to the above-mentioned evaluation of the transmittance of the spraying composition, the preparation of the aqueous composition (particulate cellulose concentration: 0.05% by weight) and the measurement of the transmittance were performed as follows.

Ion exchanged water was added to the spraying composition so as to adjust the cellulose concentration thereof to 0.05% by weight. Next, the resultant mixture was subjected to a treatment for dispersing, at 15,000 rpm for 10 minutes by means of a homogenizer (T.K. Lobo. mics™, manufactured and sold by TOKUSHU KIKA KOGYO CO., Ltd., Japan), thereby obtaining a homogenized aqueous composition. The transmittance of the aqueous composition was measured as follows. The aqueous composition was placed in a quartz cell (light path: 1 cm), and measurement was performed using a UV-visual range spectrophotometer (UV-Vis spectrophotometer UV-2500PC, manufactured and sold by SHIMADZU Corporation, Japan). The transmittance was defined as a $I_t/I_0$ ratio (in terms of a percentage (%)), wherein $I_t$ represents the transmittance intensity (=transmittance intensity of the aqueous composition), and $I_0$ represents the incident light intensity of visible rays having a wavelength of 660 nm (approximated by the transmittance intensity of light having passed through ion exchanged water (as a reference sample) placed in the same cell).

Next, the method for preparing the composition for use in the present invention is explained in detail.

As explained below, in the preparation of the spraying composition for use in the present invention, first, cellulose is dispersed in a liquid dispersion medium to thereby obtain a cellulose dispersion as a raw material (for the general purpose, the cellulose dispersion is a cellulose/water dispersion). Then, in accordance with the purpose of use of the spraying composition, a further operation is performed in which various additives are added to the cellulose dispersion, followed by stirring, and/or the cellulose dispersion is diluted with a liquid dispersion medium, followed by stirring, to thereby obtain a spraying composition.

As an example of a cellulose dispersion which can be advantageously used as a raw material for producing the composition for use in the present invention, there can be mentioned a crystalline cellulose dispersion described in Unexamined Japanese Patent Application Laid-Open Specification No. Hei 3-163135.

A dispersion of cellulose having low crystallinity can be obtained by the method described in WO99/28350. When such a dispersion of low crystallinity cellulose is used as a raw material for producing the spraying composition for use in the present invention, there is an advantage in that a spraying composition which is a gel and has high transparency can be obtained under certain conditions. Hereinbelow, a detailed explanation is made on the case where this cellulose dispersion is used as a raw material for producing the spraying composition. In this case, first, a natural or regenerated cellulose material is dissolved in an aqueous inorganic acid solution, such as sulfuric acid, and then, the cellulose material in the resultant solution is reprecipitated by using a precipitant, such as water, followed by hydrolysis under heating. The resultant hydrolysis reaction mixture is washed and concentrated to thereby remove the inorganic acid and obtain an aqueous cellulose dispersion. If desired, the dispersion medium may be replaced with an organic solvent, and the resultant dispersion may be subjected to a homogenization treatment by means of a mixer.

As mentioned above, the liquid dispersion medium contained in the cellulose dispersion is generally water. However, in accordance with the purpose of use of the spraying composition, a part or whole of the liquid dispersion medium may be replaced with a water-soluble organic solvent (such as methanol, ethanol, isopropanol, acetone, acetonitrile, dimethyl sulfoxide, dimethylformamide or dimethylacetamide), or by a mixture of these water-soluble organic solvents.

When a water-soluble organic solvent is used as the dispersion medium for preparing the cellulose dispersion, as explained above in detail in connection with the composition for use in the present invention, the water-soluble organic solvent is used in an amount of from 1 to 90% by weight, preferably from 3 to 60% by weight, more preferably from 5 to 50% by weight, based on the weight of the dispersion. When the amount of the water-soluble organic solvent is less than 1% by weight, any great effect cannot be obtained by the replacement of water with the water-soluble organic solvent. On the other hand, since the replacement of water which binds to the particulate cellulose is technically difficult, addition of the water-soluble organic solvent in an amount of more than 90% by weight is substantially impossible.

In special cases where it is desired to prepare a spraying composition containing a nonaqueous, strongly hydrophobic dispersion medium, it is necessary to use a hydrophobic organic solvent, such as a hydrocarbon (e.g., hexane or toluene) or an ester (e.g., ethyl acetate). In this case, after the removal of the inorganic acid from the above-mentioned hydrolysis reaction mixture, the water present in the resultant aqueous cellulose dispersion is replaced with a water-soluble organic solvent and, then, the water-soluble organic solvent is, in turn, replaced with a hydrophobic organic solvent. Alternatively, a water-non-soluble hydrophobic organic solvent is added to the aqueous cellulose dispersion, and the resultant mixture is subjected to a treatment for emulsification/dispersion (preliminary emulsification).

The thus-obtained cellulose dispersion as such can be used as the spraying composition for use in the present invention. Instead, the thus obtained cellulose dispersion may be used as a precursor for producing a spraying composition (of the present invention) which is adapted to a specific use; the use as a precursor can be made by, for example, any of the following methods:

a method (process A) in which an additional liquid dispersion medium and a functional additive are added, in an appropriate order, to the cellulose dispersion (as a precursor) to thereby obtain a composition, followed by a treatment for dispersing the components of the composition;

a method (process B) in which the cellulose dispersion (as a precursor) is subjected to the below-mentioned treatment for high degree pulverization, and then an additional liquid dispersion medium and a functional additive are added thereto in an appropriate order to thereby obtain a composition, followed by a treatment for dispersing the components of the composition; and a method (process C) in which an additional liquid dispersion medium and a functional additive are added, in an appropriate order, to the cellulose dispersion (as a precursor) to thereby obtain a composition, and then the composition is subjected to a preliminary treatment for dispersing the components of the composition to obtain a preliminary dispersion, followed by the below-mentioned treatment for high degree pulverization.

The method of using the cellulose dispersion as a precursor for preparing the spraying composition is not limited to these processes A to C. The method of using the cellulose dispersion as a precursor for preparing the spraying composition is not particularly limited as long as the cellulose dispersion as a precursor can be well mixed with an additional liquid dispersion medium and a functional additive, thereby obtaining a homogeneous composition.

In the case of the processes B and C mentioned above, by virtue of the operation that the precursor or the preliminary dispersion is subjected to the treatment for high degree pulverization by means of, for example, a high pressure/super high pressure homogenizer or the like, there can be obtained a more advantageous spraying composition. As an apparatus for performing the treatment for high degree pulverization, there can be mentioned, for example, Microfluidizer™ (manufactured and sold by Mizuho Kogyo Kabushiki Kaisha, Japan), Ultimaizer™ (manufactured and sold by Sugino Machine Limited, Japan) and Nanomizer™ (manufactured and sold by Yoshida Kikai Co., Ltd., Japan). For example, by using the process B (in which the precursor is subjected to the treatment for high degree pulverization), a composition for use in the present invention having more improved transparency can be obtained. On the other hand, by using the process C (in which the preliminary dispersion is subjected to the treatment for high degree pulverization), there can be obtained an emulsion containing oil globules having a very small size of a submicron level (or water globules having a very small size of a submicron level, depending on the production conditions). In many cases, such an emulsion is white opaque. The treatment for high degree pulverization may be conducted two or more times.

For the treatment for dispersing conducted in the processes A and B and for the preliminary treatment for dispersing conducted in the process C, various machines conventionally used for treatments for mixing and/or dispersing can be used. Specifically, there can be used kneading machines, such as a vacuum homomixer, a disperser, a propeller mixer and a kneader; various grinders; a blender; a homogenizer; an ultrasonic emulsifier; a colloid mill; a pebble mill; a ball mill; a planetary ball mill; a bead mill and a high pressure homogenizer.

An appropriate treatment for mixing and/or dispersing can be selected in accordance with the purpose of use of the spraying composition and the formulation of the spraying composition. The operation conditions for preparing the composition (such as the temperature, the conditions for dispersing, and the order of adding the additives) are appropriately selected in accordance with the formulation of the composition. For example, when two or more functional additives are used in combination, it may be effective to introduce the functional additives by a method in which, depending on the solubility and precipitation properties of the additives, the additives are preliminarily dissolved in a liquid dispersion medium to obtain a solution and, then, the obtained solution is added to the composition. The composition used in the present invention has a characteristic that it is a viscous composition, irrespective of whether it is a highly transparent composition or an opaque composition (such as an emulsion or a pigment dispersion). Therefore, in many cases, the composition used in the present invention (obtained by the above-mentioned treatment for dispersing) is likely to contain many bubbles. In such case, it is effective to conduct a vacuum deaeration treatment at the end of the production process or add an antifoaming agent, such as ethanol, to the composition.

The pH value of the composition is in the range of from 2.0 to 11.0, preferably from 3.0 to 10.0, more preferably from 3.5 to 9.5. When the pH value of the composition is in the above-mentioned range, a highly homogenous spraying composition having excellent stability can be obtained. On the other hand, when the pH value of the composition is less than 2.0 or greater than 11.0, cellulose, which is an essential component of the composition, is likely to aggregate and cause adverse effects on the homogeneity and stability of the composition. The pH value of the composition for use in the present invention can be controlled so as to fall within the above-mentioned range by appropriately adding to the composition an inorganic acid, an inorganic salt, an organic acid or an organic salt.

Hereinbelow, an explanation is made on the method for producing a spraying composition which contains an oil component or a mixture of two or more oil components as an additive, i.e., a spraying composition in the form of an oil-in-water emulsion (hereinafter, frequently referred to as an "O/W emulsion").

With respect to the cellulose used in the present invention, the cellulose itself is emulsifiable and, thus, an emulsion can be prepared without using a surfactant. When a surfactant is used as an emulsifier, cellulose functions as an emulsion stabilizer.

An emulsion can be prepared in accordance with a conventional method for preparing an O/W emulsion.

For example, an emulsion can be prepared as follows. An aqueous dispersion of low crystallinity particulate cellulose is prepared in the above-mentioned manner. An oil component or a mixture of two or more oil components is mixed with the aqueous cellulose dispersion at 70 to 80° C., and the resultant mixture is emulsified. The emulsification can be conducted by means of a conventional emulsifier or an apparatus which is capable of effecting a more powerful emulsification, such as a high pressure homogenizer or a super high pressure homogenizer. Thus, the composition for use in the present invention is obtained which is an emulsion containing an oil component or a mixture of two or more oil components as an additive.

By the above-mentioned method, an emulsion can be obtained without using any surfactant. When a surfactant is used which is a conventional emulsifier and, also, low crystallinity particulate cellulose is used as an auxiliary emulsifier (emulsion stabilizer), an emulsion can also be prepared in the similar manner.

Further, a stable emulsion in the form of a gel can be obtained by a method in which an aqueous gel containing cellulose, and an O/W emulsion containing no cellulose, are separately prepared and, then, the gel and the emulsion are mixed together.

The cellulose-containing composition for use in the present invention which is produced by the above-mentioned method is either a transparent dispersion or a translucent or opaque dispersion.

When the composition is a transparent dispersion containing almost no foamable surfactant, such as a non-ionic surfactant (which does not lower the transparency of the composition), such a composition can produce excellent mist. On the other hand, when the composition contains at least a predetermined amount of a foamable surfactant, such as a nonionic surfactant (which does not lower the transparency of the composition), such a composition can function as a special embodiment of the present invention, namely a so-called foaming composition which produces a foam when the composition is extruded from a spray container device. In this case, due to the network formed by the particulate cellulose contained in the foam, the foam exhibits very high stability, thereby exhibiting the excellent effects of the present invention as a foamable spraying composition.

With respect to the translucent or opaque dispersion, it is considered that a dispersion becomes translucent or opaque when, for example, one of the following cases applies: a case where cellulose contained in the dispersion has a particle diameter on the micrometer order; a case where cellulose forms a loose aggregation; a case where an O/W emulsion is formed by an oil compound used as one of the components; a case where the dispersion contains a microparticulate component which is insoluble in the dispersion medium and which has a particle size which induces light scattering; and a case where the dispersion contains at least a predetermined amount of a foamable ionic surfactant (in this case, loss of transparency of the composition is caused by the loose aggregation of cellulose). Except for the case where the composition is a dispersion containing a foamable ionic surfactant in at least a predetermined amount, the composition in any case can produce excellent mist. When the composition is a dispersion containing a foamable ionic surfactant in at least a predetermined amount, the composition can function advantageously as a foamable spraying composition.

In the present invention, the above-mentioned composition is packed in a spray container device to obtain a spray pack.

With respect to the spray container device used in the present invention, there is no particular limitation. Any spray container device can be used as long as the device is capable of being easily packed with the composition and spraying the composition, and the packed composition is capable of functioning as a spraying composition. However, from the viewpoint of the general-purpose properties and the high accuracy of spraying, the following three types of spray container devices are especially preferred.

One of the preferred spray container devices used in the present invention is a dispenser type spray container device equipped with a pump type nozzle which is capable of spraying under conditions wherein the internal pressure of the container is maintained at atmospheric pressure. Such a spray container device is capable of forming mist under atmospheric pressure without using a pressurized gas or the like. Further, this container device has a relatively simple structure and has high safety and high portability. This spray container device is composed of a screw type container which is for accommodating the composition packed therein and which has, fitted at its inlet, an extrusion pump type nozzle equipped with a suction tube placed inside of the container. The term "dispenser type spray container device" used herein is intended to cover all such devices inclusive of improved devices having a pump type nozzle which is modified for improving the spraying performance thereof. The spraying performance of a spray container device varies depending on the hole diameter of the spraying nozzle and the extrusion volume of the pump, and these conditions are selected in accordance with the purpose of use of the spray pack.

Since the average particle diameter of the cellulose which is contained in the composition packed in the spray container device is 10 μm or less, in general, clogging of the nozzle hole is unlikely to occur under the conditions for using the spray container device (i.e., the inner diameter of the nozzle is about 50 to 1,000 μm), and therefore the spraying (or foaming) can be performed without any problems. In addition, since the composition used in the present invention has a property such that the viscosity thereof is lowered when only a very small amount of stress is applied, drawing up of the composition through the suction tube can be performed satisfactorily when the inner diameter of the suction tube is about 0.1 mm or more.

The above-mentioned conditions with respect to the nozzle and the suction tube also apply to the below-mentioned other two types of spray container devices.

A trigger type spray container device is also preferred in the present invention. A trigger type spray container device is suitable for the spraying of household detergents, textile starches, kitchen detergents and the like, and it is composed of a container which is for accommodating the composition packed therein and which has, fitted at its inlet, a pistol-shaped, trigger type spray device. Like the dispenser type spray container device, this spray container device is capable of spraying under conditions wherein the internal pressure of the container is maintained at atmospheric pressure, and this spray container device has high general-purpose properties for the spraying of a liquid. The term "trigger type spray container device" used herein is intended to cover all such devices inclusive of improved devices which are modified for improving the spraying performance thereof. As mentioned above, the spraying composition used in the present invention is a highly viscous composition which may be in the form of a gel. Irrespective of whether or not the composition is a gel, the composition used in the present invention is advantageous in that, as in the case of the dispenser type spray container device, by the use of a spray pack obtained by packing the composition used in the present invention into a trigger type spray container device, excellent spray (or foam) can be produced under any operation conditions.

In addition, an aerosol spray container device can be mentioned as another example of a preferred spray container device used in the present invention. In the case of the use of an aerosol spray container device, an aerosol propellant is packed in the container together with the spraying composition. By virtue of the use of the aerosol propellant, an aerosol spray container device enables continuous spraying or continuous formation of foam, which cannot be realized by the above-mentioned two types of devices. The term "aerosol spray container device" used herein is intended to cover all such devices inclusive of improved devices which are modified for improving the spraying performance thereof. Use of an aerosol spray container device is preferred especially when the spraying composition used in the present invention is used as a foaming composition. In general, the use of an aerosol spray container device enables the formation of a finer spray than in the case of the use of the above-mentioned other two types of spray container devices, which are operated under conditions wherein the internal pressure of the container is maintained at atmospheric pressure. Examples of aerosol propellants used in the present invention include dimethyl ether, liquefied petroleum gas, carbon dioxide gas, nitrogen gas, argon gas, air, oxygen gas and flon gas (chlorofluorocarbon gas). However, the aerosol propellant is not limited to these gases. These gases can be used individually or in combination. The aerosol propellant is selected taking into consideration various factors, and one of the criteria for selecting the aerosol propellant is the solubility of the aerosol propellant in the liquid dispersion medium of the spraying composition. For example, when a large part of the dispersion medium is a strongly hydrophobic organic solvent (such as isopropanol or n-hexane), a liquefied petroleum gas is preferred as an aerosol propellant. When the water content of the spraying composition is high, dimethyl ether is preferred as an aerosol propellant.

With respect to the use of any spray container device, the cellulose-containing composition used in the present invention is advantageous in that, when the composition is formulated so as to exhibit a high viscosity enough to take a gel form, to thereby prevent the composition from flowing in the inside of the container, the spraying (or formation of foam) can be performed in any direction. In an extreme case, such a spray pack of the present invention can be used even when the spray pack is held upside down.

BEST MODE FOR CARRYING OUT THE INVENTION

Hereinbelow, the present invention will be described in more detail with reference to the following Examples and Comparative Examples, but they should not be construed as limiting the scope of the present invention.

First, an explanation is made with respect to the methods for evaluating the compositions prepared in the Examples and the Comparative Examples.

The structural parameters and the properties were evaluated by the following methods.

(1) Characterization of Cellulose in a Composition

① The measurement of a wide-angle X-ray diffraction pattern was performed using an X-ray diffraction apparatus (RU-300, a lint system is attached thereto; manufactured and sold by Rigaku Corporation, Japan), and then $x_I$ and $x_{II}$ were determined by the above-mentioned method.

② The average particle diameter of particulate cellulose was determined by the above-mentioned method using the Laser Diffraction/Scattering Type Particle Size Measuring Apparatus LA-920 (manufactured and sold by HORIBA Ltd., Japan).

③ The average degree of polymerization (DP) was evaluated by the following method. A dried cellulose sample was dissolved in cadoxene to obtain a diluted cellulose solution. The specific viscosity of the diluted cellulose solution was measured at 25° C. using an Ubbellohde viscometer. From the specific viscosity, an intrinsic viscosity value [η] was obtained. From the intrinsic viscosity value [η], a weight average degree of polymerization (DP) was calculated.

(2) Viscosity of a Composition ($\eta_{max}$)

The viscosity ($\eta_{max}$) was measured using a cone-plate type rotating viscometer (RS-100, manufactured and sold by Haake Company, German) under conditions wherein cone angle: 4°; plate diameter: 35 mm; the shear rate (γ') region: from $1\times10^{-3}$ s$^{-1}$ to $1\times10^2$ s$^{-1}$, and the measuring temperature: 25° C.

(3) Relative Transmittance of a Diluted Composition to Visible Rays Having a Wavelength of 660 nm A composition was diluted with water to have a particulate cellulose concentration of 0.05% by weight (wherein, when a viscosity modifier other than cellulose was employed, the concentration of the viscosity modifier employed was adjusted to 0.05% by weight). The resultant aqueous composition was subjected to a treatment for dispersing, at a revolution rate of 15,000 rpm for 10 minutes by means of a homomixer (T. K. ROBO MICS™, manufactured and sold by TOKUSHU KIKA KOGYO Co., Ltd., Japan), to thereby obtain a diluted aqueous composition. The relative transmittance of the diluted aqueous composition was measured by means of a UV-visual range spectrophotometer (UV-2500PC, manufactured and sold by SHIMADZU Corporation, Japan).

(4) Evaluation of the Spraying Properties

With respect to the spraying properties of various spraying compositions, the following evaluations were performed.

① State of spray; a spraying was performed and the state of the spray was evaluated in accordance with the following criteria.

The spraying composition cannot be shot from the nozzle, that is, a spraying cannot be performed. →X Although the spraying composition can be shot from the nozzle, the spraying composition cannot form a mist. →Δ

The spraying composition can be shot from the nozzle and form an excellent mist. →○

② unevenness in spray coating; A frosted glass plate having a size of 18 cm×18 cm was vertically disposed. A spraying was performed once toward the glass plate, from a position which was at a horizontal distance of 20 cm from the frosted glass plate, and the distribution of droplets which attached to the surface of the frosted glass plate was observed immediately after the spraying. The unevenness in the spray coating was evaluated in accordance with the below-mentioned criteria, as compared to the results of a spraying which was performed in the same manner as mentioned above except that ion-exchanged water was used instead of the spraying composition.

The spray coating on the frosted glass plate is interspersed with large droplets and, thus, a marked unevenness in the spray coating is observed. →X Although the spray coating on the frosted glass plate is not interspersed with large droplets, the distribution of the droplets is much more rough than in the case of the spraying of ion-exchanged water. →Δ

The distribution of droplets is as dense as or more dense than in the case of the spraying of ion-exchanged water. →○

③ Anti-dripping properties; Under the same conditions as in the spraying for the evaluation of the unevenness in the spray coating, a spraying was performed several times until the overall surface of the frosted glass plate (which was held vertically) was completely covered with the sprayed composition. The anti-dripping properties of the sprayed composition on the frosted glass plate (which was maintained in a vertical position) was observed after every spraying and was evaluated in accordance with the following criteria.

A dripping occurs even after only one spraying. →X

Although a dripping does not occur after the first spraying, a dripping occurs after two or more sprayings are performed to increase the thickness of the spray coating on the surface of the frosted glass plate. →Δ

No dripping occurs even after the spraying is repeated until the overall surface of the frosted glass plate was completely covered with the sprayed composition. →○

④ Coating formation ability; A spraying was performed several times under the same conditions as in the spraying for the evaluation of the unevenness in the spray coating. The spray coating formed on the surface of the frosted glass plate was, as such, allowed to dry at room temperature to obtain a coated glass. The state of the surface of the obtained coating on the glass was observed and was evaluated in accordance with the following criteria.

The surface of the coating exhibits high uniformity (no rough feel), and even when the surface of the coating is rubbed by finger, the coating cannot be peeled off. →○

The surface of the coating exhibits a markedly rough feel; or even if the surface of the coating exhibits high uniformity, when the surface of the coating is rubbed by finger, the coating can be easily peeled off. →X

EXAMPLES 1 TO 7

With respect to a spraying composition comprising a cellulose/water dispersion, the spraying properties were examined as follows.

(1) Preparation of a Cellulose/Water Dispersion

A sheet form of purified pulp was cut into chips having a size of 5 mm×5 mm A, to thereby obtain a raw material pulp having a degree of polymerization of 760 (hereinbelow referred to simply as a "purified pulp"). The purified pulp was dissolved in a 65% by weight aqueous sulfuric acid solution at −5° C. so as to obtain a cellulose concentration of 5% by weight, thereby obtaining a transparent and viscous cellulose dope. The cellulose dope was poured, while stirring, into water (at 5° C.) in an amount about 2.5 times the weight of the cellulose dope, to thereby aggregate the cellulose to form a floc, thereby obtaining a suspension of a floc form of solids. The obtained suspension was subjected to hydrolysis at 85° C. for 20 minutes, and then the aqueous sulfuric acid solution as a dispersion medium was removed from the suspension by vacuum filtration using a fritted-glass filter, to obtain solids. The obtained solids were repeatedly subjected to washing until the pH value of the washings became about 3 and then washed (neutralized) with a thin aqueous ammonia solution having a pH value of about 11, followed by further washing thereof with ion-exchanged water, to thereby obtain a white opaque, gel-like product having a cellulose content of 6.0% by weight. The gel-like product was diluted with ion-exchanged water so as to adjust the cellulose content thereof to 4.0% by weight. The resultant diluted product was subjected to a treatment for dispersing, at a revolution rate of 15,000 rpm for 10 minutes by means of a homomixer (T. K. ROBO MICS™, manufactured and sold by TOKUSHU KIKA KOGYO Co., Ltd., Japan), and then subjected 5 times to a treatment for dispersing, under a pressure of $1.72×10^8$ Pa by means of an ultrahigh pressure homogenizer (Microfluidizer™ Model M110-EH, manufactured and sold by Mizuho Kogyo Kabushiki Kaisha, Japan), to thereby obtain a cellulose/water dispersion (pH=6.7) exhibiting a high transparency. The obtained cellulose/water dispersion having a cellulose content of 4.0% by weight is hereinafter referred to as "sample A". FIG. 1 shows a wide-angle X ray pattern of a dried product obtained from sample A.

The cellulose of the sample A had an average degree of polymerization of 38, a crystallinity such that $X_I$ was 0 and $X_{II}$ was 0.18, and an average particle diameter of 0.3 μm.

(2) Preparation of the Samples S1 to S7 and Evaluation of the Spraying Properties Ion-exchanged water was added to the sample A so as to prepare four diluted samples having cellulose contents of 0.5% by weight, 1.0% by weight, 1.5% by weight and 2.0% by weight, respectively. Each of the diluted samples was individually subjected to a treatment for dispersing, at a revolution rate of 15,000 rpm for 10 minutes by means of a homomixer (T. K. ROBO MICS™, manufactured and sold by TOKUSHU KIKA KOGYO Co., Ltd., Japan) to obtain four cellulose/water dispersions which were spraying compositions used in the present invention. These dispersions were, respectively, designated samples "S1", "S2", "S3" and "S4" in the order from the sample having the lowest cellulose content to the sample having the highest cellulose content. The transmittances of these samples to visible rays having a wavelength of 660 nm were 99% (S1), 98% (S2), 96% (S3) and 93% (S4), as measured in the state in which they were individually diluted with water to have a particulate cellulose concentration of 0.05% by weight. The maximum viscosity values ($\eta_{max}$) of the samples S1, S2, S3 and S4 at 25° C. were $2\times10^3$ mPa·s (S1), $2\times10^5$ mPa·s (S2), $2\times10^6$ mPa·s (S3) and 5 (107 mPa·s (S4). FIGS. 2 and 3 are graphs which show specific examples of measurement data for evaluating the maximum viscosity ($\eta_{max}$) defined in the present invention, wherein the data was obtained, with respect to the sample S3 by using a cone-plate type rotating viscometer.

A commercially available crystallite cellulose/water dispersion, namely Ceolus FP-03™ (cellulose content: 10% by weight, manufactured and sold by ASAHI KASEI CORPORATION, Japan) was diluted with ion-exchanged water so as to adjust the cellulose content thereof to 4.0% by weight, and then subjected to a treatment for dispersing, at a revolution rate of 15,000 rpm for 10 minutes by means of a homomixer (T. K. ROBO MICS™, manufactured and sold by TOKUSHU KIKA KOGYO Co., Ltd., Japan) to obtain a cellulose/water dispersion (sample S5).

Next, Ceolus FP-03™ was diluted with ion-exchanged water so as to adjust the cellulose content thereof to 2.0% by weight, and then subjected to a treatment for dispersing, at a revolution rate of 15,000 rpm for 10 minutes by means of a homomixer (T. K. ROBO MICS™, manufactured and sold by TOKUSHU KIKA KOGYO Co., Ltd., Japan) to obtain a cellulose/water dispersion. The obtained cellulose/water dispersion was subjected 5 times to a treatment for dispersing, under a pressure of $1.72\times10^8$ Pa by means of an ultrahigh pressure homogenizer (Microfluidizer™ Model M110-EH, manufactured and sold by Mizuho Kogyo Kabushiki Kaisha, Japan), to thereby obtain a white opaque cellulose/water dispersion (sample S6).

Each of the celluloses of the samples S5 and S6 had a degree of polymerization of 150 and a crystallinity such that $X_I$ was 0.65 and $X_{II}$ was 0. The celluloses of the samples S5 and S6 had average particle diameters of 5.2 μm and 0.2 μm, respectively. The transmittances of the samples 5S and S6 to visible rays having a wavelength of 660 nm were, respectively, 0.3% and 26%, as measured in the state in which they were individually diluted with water to have a particulate cellulose concentration of 0.05% by weight. The maximum viscosity values ($\eta_{max}$) of the samples S5 and S6 were $6\times10^4$ mPa·s and $7\times10^4$ mPa·s, respectively.

A commercially available cuprammonium rayon long fiber was finely cut into a length of 1 mm, and the resultant was hydrolyzed in a 30% aqueous sulfuric acid solution at 80° C., for 2 hours to obtain a dispersion. The obtained dispersion was subjected to filtration using a fritted-glass filter, followed by repetition of washing with ion-exchanged water until the pH value of the washings became about 4, thereby obtaining a cake. The obtained cake was neutralized by means of a diluted ammonia aqueous solution having a pH value of about 11, followed by washing thereof with ion-exchanged water to thereby obtain a dispersion. The obtained dispersion was diluted with ion-exchanged water so as to adjust the cellulose content thereof to 2.0% by weight and then subjected to a preliminary treatment for dispersing, at a revolution rate of 15,000 rpm for 10 minutes by means of a homomixer (T. K. ROBO MICS™, manufactured and sold by TOKUSHU KIKA KOGYO Co., Ltd., Japan), and then subjected 5 times to a treatment for dispersing, under a pressure of $1.72\times10^8$ Pa by means of an ultrahigh pressure homogenizer (Microfluidizer™ Model M110-EH, manufactured and sold by Mizuho Kogyo Kabushiki Kaisha, Japan), to thereby obtain a slightly whitish opaque cellulose/water dispersion having a cellulose content of 2.0% by weight (sample 7).

The cellulose of the sample 7 had an average degree of polymerization of 42, a crystallinity such that $X_I$ was 0 and $X_{II}$ was 0.52, and an average particle diameter of 0.3 μm. The transmittance of the sample S7 to visible rays having a wavelength of 660 nm was 65%, as measured in the state in which sample S7 was diluted with water to have a particulate cellulose concentration of 0.05% by weight. The maximum viscosity value ($\eta_{max}$) of the sample S7 was $8\times10^4$ mPa·s.

Each of the thus-obtained dispersions (samples 1 to 7) was individually packed in a commercially available dispenser-type spray container device having a volume of 50 ml (manufactured and sold by SANPLATEC Corp., Japan), and subjected to evaluation of the spraying properties. The results are shown in Table 1.

It was found that all of the samples 1 to 7 exhibited excellent spraying properties.

It is necessary for the spraying composition used in the present invention to have an advantage in that, after spraying and drying, the spraying composition can form an excellent coating. Therefore, the coating formation abilities (after drying) of the samples 1 to 7 were examined. It was found that each of the coatings formed from the samples S1 to S7 exhibited high uniformity (no rough feel) and that, even when each of the coatings was rubbed by finger, the coatings could not be peeled off, thereby confirming that a strong coating was formed. The results are shown in Table 1.

COMPARATIVE EXAMPLES 1 TO 7

(Preparation of the Samples H1 to H7 and Evaluation of the Spraying Properties)

As described hereinbelow, evaluation of spraying properties was performed with respect to each of a cellulose dispersion which did not satisfy the requirements of the present invention, an aqueous polymer solution, and a microparticle dispersion.

A crystalline cellulose powder, namely Avicel PH-101™ was dispersed in ion-exchanged water so that the resultant dispersion had a cellulose content of 5% by weight, and the obtained dispersion was subjected to a treatment for dispersing, at a revolution rate of 15,000 rpm for 10 minutes by means of a homomixer (T. K. ROBO MICS™, manufactured and sold by TOKUSHU KIKA KOGYO Co., Ltd., Japan) to obtain a white cellulose/water dispersion (sample H1).

The sample H1 exhibited a property such that when the sample H1 was allowed to stand for several minutes, a transparent supernatant was formed therein, indicating that the sample H1 was an inhomogeneous, incomplete dispersion.

The cellulose of the sample Hi had an average degree of polymerization of 150, a crystallinity such that $X_I$ was 0.64 and $X_{II}$ was 0, and an average particle diameter of 21 μm. The transmittance of the sample H1 to visible rays having a wavelength of 660 nm was almost 0%, as measured in the state in which the sample H1 was diluted with water to have a particulate cellulose concentration of 0.05% by weight. The maximum viscosity value ($\eta_{max}$) of the sample H1 was $1 \times 10^3$ mPa·s. With respect to the measurement of the transmittance and the $\eta_{max}$ value of the sample H1, the sample H1 was strongly shaken just before the measurement, and the measurement was then performed quickly.

Further, as additional comparative samples, aqueous solutions and aqueous dispersions were prepared by a method in which each of the following raw materials: a crosslinked acrylic copolymer (namely Carbopol 940™ (sold by Chugai Boyeki Co., Ltd., Japan)), a polyacrylamide (average molecular weight: 9,000,000 to 10,000,000; manufactured and sold by KISHIDA CHEMICAL CO., LTD., Japan), and a particulate synthetic smectite (namely SMECTON SA2™ (manufactured and sold by KUNIMINE INDUSTRY, Japan)), was individually dissolved or dispersed in ion-exchanged water used as a solvent or a dispersion medium so that, from each raw material, two aqueous mixtures were obtained which had raw material contents of 0.5% by weight and 1.5% by weight, respectively.

With respect to Carbopol and a polyacrylamide, the aqueous solutions thereof were prepared by the conventional method (wherein, in the preparation of the aqueous solutions of Carbopol, after dissolving Carbopol in water, neutralization with a diluted aqueous ammonia was performed). The 0.5% by weight aqueous solution of Carbopol (in the form of a gel) was designated "sample H2", and the 1.5% by weight aqueous solution of Carbopol (in the form of a gel) was designated "sample H3". The 0.5% by weight aqueous solution of polyacrylamide (in the form of a solution) was designated "sample H4", and the 1.5% by weight aqueous solution of polyacrylamide (in the form of a solution) was designated "sample H5".

With respect to the use of SMECTON SA2™, SMECTON SA2™ was diluted with ion-exchanged water so that the resultant mixtures had SMECTON SA2™ concentrations of 0.5% by weight and 1.5% by weight, respectively, and then the obtained mixtures were individually subjected to a treatment for dispersing, at a revolution rate of 15,000 rpm for 10 minutes by means of a homomixer (T. K. ROBO MICS™, manufactured and sold by TOKUSHU KIKA KOGYO Co., Ltd., Japan) to obtain transparent aqueous dispersions.

The 0.5% by weight SMECTON SA2™ dispersion was designated "sample H6" and the 1.5% by weight SMECTON SA2™ dispersion was designated "sample H7". The transmittances of the samples H2 to H7 to visible rays having a wavelength of 660 nm were 99% or more (H2, H3, H4 and H5), 89% (H6) and 72% (H7), as measured in the state in which the samples were individually diluted with water to have a raw material concentration of 0.05% by weight. The maximum viscosity values ($\eta_{max}$) of the samples H2 to H7 at 25° C. were $3 \times 10^6$ mPa·s (H2), $1 \times 10^7$ mPa·s (H3), $4 \times 10^2$ mPa·s (H4), $4 \times 10^4$ mPa·s (H5), $3 \times 10^2$ mPa·s (H6) and $1 \times 10^6$ mPa·s (H7). Each of the thus obtained dispersions or aqueous solutions (H1 to H7) was individually packed in a commercially available dispenser type spray container device having a volume of 50 ml (manufactured and sold by SANPLATEC Corp., Japan), and subjected to evaluation of the spraying properties. The results are shown in Table 1.

In the case of the sample H1, which was a dispersion containing a particulate cellulose having a relatively large particle diameter, the particulate cellulose caused a temporary clogging of the nozzle, and therefore a stable spraying could not be achieved. Also, the unevenness in the spray coating was large. Further, with respect to the aqueous solutions which contained Carbopol or polyacrylamide dispersed (dissolved) therein in the molecular form, a spraying from the spray container device could not be performed irrespective of the concentrations of these aqueous solutions, and therefore it was shown that the viscous aqueous solutions containing Carbopol or polyacrylamide were unsuitable as a spraying composition. On the other hand, the dispersion of SMECTON exhibited good spraying properties; however, from the viewpoint of the anti-dripping properties, the dispersion of SMECTON was not satisfactory. When the coating formation abilities of the samples H1 to H7 were examined by substantially the same method as in the evaluation of the samples S1 to S7, it was found that the sample H1 formed a white coating giving a markedly rough feel, and that the samples H2 to H7 formed coatings which were transparent and which exhibited a high uniformity. When these coatings were rubbed by finger, although no peeling off was observed in the case of the coatings formed from the samples H1 to H5, the coatings formed from the samples H6 and H7 were easily peeled off from the glass plate and the resultant powdery debris of the coatings stuck to the finger. Thus, it was found that although the dispersion of the SMECTON exhibited good spraying properties, the coating formation ability of the dispersion of the SMECTON was very poor, as compared to the spraying composition used in the present invention. The results are shown in Table 1.

EXAMPLE 8 AND COMPARATIVE EXAMPLE 8

In order to show the difference between the spraying composition used in the present invention and a dispersion of the synthetic smectite, the following experiments were performed.

Ion-exchanged water and ethanol were added to the above-mentioned sample A so that the resultant mixture had a cellulose content of 2% by weight and an ethanol/water weight ratio of 30/70 (g/g), and then the obtained mixture was subjected to a treatment for dispersing, at a revolution rate of 15,000 rpm for 10 minutes by means of a homomixer (T. K. ROBO MICS™, manufactured and sold by TOKUSHU KIKA KOGYO Co., Ltd., Japan) to thereby obtain a transparent aqueous dispersion (sample S8).

Likewise, ion-exchanged water and ethanol were added to SMECTON SA2™ so that the resultant mixture had a SMECTON SA2™ content of 2% by weight and an ethanol/water weight ratio of 30/70 (g/g), and then the obtained mixture was subjected to a treatment for dispersing, at a revolution rate of 15,000 rpm for 10 minutes by means of a homomixer (T. K. ROBO MICS™, manufactured and sold by TOKUSHU KIKA KOGYO Co., Ltd., Japan) to thereby obtain a white opaque aqueous dispersion (sample H8).

The transmittances of the thus-obtained samples S8 and H8 to visible rays having a wavelength of 660 nm were 92% (S8) and 2% (H8), as measured in the state in which the samples S8 and H8 were individually diluted with water to have a particulate cellulose concentration of 0.05% by weight and a SMECTON SA2™ concentration of 0.05% by weight, respectively. The maximum viscosity values ($\eta_{max}$) of the samples S8 and H1 at 25° C. were $6 \times 10^7$ mPa·s (S8) and $1 \times 10^6$ mPa·s (H8).

Each of the samples S8 and H8 was individually packed in a commercially available dispenser type spray container device having a volume of 50 ml (manufactured and sold by SANPLATEC Corp., Japan), and subjected to evaluation of the spraying properties. The results are shown in Table 2. Each of the samples S8 and H8 exhibited excellent spraying properties.

Next, the coating formation abilities of the samples S8 and H8 were examined by the above-mentioned method. It was found that the coating formed from the sample S8 was transparent, and even when the coating was rubbed by finger, no peeling off of the coating occurred. On the other hand, the coating formed from the sample H8 was opaque and also rough and non-uniform, where the roughness and non-uniformity indicated that weak agglomeration of SMECTON SA2™ occurred during the drying of the sprayed sample H8 on the glass plate.

Further, when the coating formed from the sample H8 was rubbed by finger, the white opaque coating was easily peeled off from the glass plate and the resultant powdery debris of the coating stuck to the finger. For comparison with the coating formed from the sample H8, the coating formed from a SMECTON/water dispersion having a SMECTON content of 1.5% by weight and exhibiting a relatively high transparency, was observed (wherein the coating was obtained in Comparative Example 7). It was found that the coating obtained in Comparative Example 7 exhibited high transparency (although the thickness of the coating was non-uniform because of the occurrence of dripping in accordance with the lapse of time); however, when this transparent coating was rubbed by finger, a powder of smectite easily came off, as in the case of the sample H8. Thus, it was found that a synthetic somectite exhibits a lower agglomeration during the drying of the wet coating, than in the case of a particulate cellulose, and therefore it is difficult for a synthetic smectite dispersion to form a continuous dry coating, that is, a synthetic smectite dispersion has almost no coating formation ability.

Thus, the following was found. When a dispersion of an inorganic particle, such as a synthetic smectite, is used as a spraying composition, dripping (after spraying) can be prevented to some degree. However, the dispersion of an inorganic particle has a defect in that when a dispersion medium having high general-purpose properties, such as alcohol, is added to the inorganic particle, agglomeration of the inorganic particle occurs, and also a coating formed from the dispersion becomes non-uniform and can be easily peeled off from the glass plate, making it impossible to produce a functional durable coating.

EXAMPLES 9 TO 11

In order to illustrate the composition for use in the present invention containing an ionic compound as a functional additive, the following experiments were performed. A composition for use in the present invention was prepared containing, as a functional additive, an ionic compound, namely betaine (N-trimethylglycin, represented by the formula: $(CH)_3 N^+CH_2CO^-$), which is an amphoteric humectant. The composition was evaluated with respect to the stability, spraying properties and coating formation ability thereof. In the experiments, three compositions were prepared as follows:
sample S9: cellulose: 1.5% by weight
betaine: 0.5% by weight
water: balance
sample S10: cellulose: 1.5% by weight
betaine: 0.5% by weight
ethanol: 10% by weight
water: balance
sample S11: cellulose: 1.5% by weight
betaine: 6% by weight
water: balance

| sample S9: | cellulose: | 1.5% by weight |
|---|---|---|
| | betaine: | 0.5% by weight |
| | water: | balance |
| sample S10: | cellulose: | 1.5% by weight |
| | betaine: | 0.5% by weight |
| | ethanol: | 10% by weight |
| | water: | balance |
| sample S11: | cellulose: | 1.5% by weight |
| | betaine: | 6% by weight |
| | water: | balance |

The samples were prepared by the following method.

Predetermined amounts of a betaine, an ethanol (only for producing sample S10) and ion-exchanged water were added to the above-mentioned sample A in accordance with the above-mentioned formulations. The resultant mixtures were individually subjected to a treatment for dispersing, at a revolution rate of 10,000 rpm and at room temperature (under cooling) for 10 minutes, by means of a vacuum emulsification equipment (PVQ-3UN, manufactured and sold by Mizuho Kogyo Kabushiki Kaisha, Japan), followed by vacuum defoaming, thereby obtaining the samples as mentioned above. The obtained three samples S9 to S11 were evaluated, and it was found that the maximum viscosity values ($\eta_{max}$) of samples S9 to S11 at 25° C. were $3\times10^5$ mPa·s (S9), $8\times10^5$ mPa·s (S10) and $7\times10^5$ mPa·s (S18), respectively; and the transmittances of samples S9 to S11 to visible rays having a wavelength of 660 nm were 96% (S9), 91% (S10) and 93% (S11), as measured in the state in which the samples were individually diluted with water to have a particulate cellulose concentration of 0.05% by weight.

with respect to homogeneity and whether or not phase separation occurred, each sample was examined both immediately after the preparation thereof and after each sample was allowed to stand still for 24 hours at room temperature from the preparation thereof. As a result, it was found that each sample was homogeneous and exhibited no phase separation at any time point the examination was made. Thus, it was found that the three compositions as mentioned above had desired properties with respect to homogeneity and stability. Further, samples S9 to S11 were individually examined with respect to the state of spray, unevenness in spray coating, and anti-dripping properties (after spraying), in substantially the same manner as in the evaluation of samples S1 to S8. As a result, it was found that each sample exhibited excellent properties (evaluation symbol ◯) in all these items of evaluation. Further, samples S9 to S11 were individually evaluated with respect to the coating forming ability thereof in substantially the same manner as in Examples 1 to 7. As a result, it was found that each of the coatings formed from samples S9 to S11 exhibited high uniformity (no rough feel) and that, even when each of the coatings was rubbed by finger, the coatings could not be peeled off, thereby confirming that a strong coating was formed.

From these results, it was found that the three compositions as mentioned above can be advantageously used because they exhibit excellent properties with respect to all of stability, spraying properties and coating formation ability.

EXAMPLE 12

Using the above-mentioned sample A, a spray pack was produced containing a cosmetic whitening gel spray composition having a whitening effect, which had the following formulation:

| | |
|---|---|
| dipropylene glycol (humectant): | 5.0% by weight |
| polyethylene glycol (humectant): | 5.0% by weight |
| ethanol: | 10.0% by weight |
| polyoxyethylene sorbitan monostearate (surfactant): | 1.0% by weight |
| sorbitan monooleate (surfactant): | 0.5% by weight |
| oleyl alcohol (emollient): | 0.5% by weight |
| placenta extract (medicine): | 0.2% by weight |
| vitamin E acetate (medicine): | 0.2% by weight |
| a perfume, an antiseptic agent and an anti-discoloration agent: | appropriate amounts |
| sample A: | 37.5% by weight |
| purified water: | 39.3% by weight |

(Production Method)

Purified water was added to sample A. The resultant mixture was subjected to a treatment for dispersing, at a revolution rate of 7,000 rpm by means of a homomixer (T.K. ROBO MICS™, manufactured and sold by Tokushu Kika Kogyo Co., Ltd., Japan), and the humectants and anti-discoloration agent were consecutively added to and dissolved in the mixture while effecting the treatment for dispersing, followed by a further treatment for dispersing for 10 minutes, thereby obtaining an aqueous gel. On the other hand, the emollient, medicines and antiseptic agent were dissolved into ethanol, and the resultant solution was added to the above-mentioned aqueous gel, and the resultant mixture was subjected to a microemulsification at a revolution rate of 10,000 rpm by means of the homomixer, followed by deaeration and filtration, thereby obtaining a translucent gel-like composition. The obtained translucent gel-like composition was packed in a 50 ml volume dispenser type spray container device (manufactured and sold by SANPLATEC Corp., Japan). The obtained gel-like composition is hereinafter referred to as "sample S12". The transmittance of sample S12 to visible rays having a wavelength of 660 nm was 34%, as measured in the state in which sample S12 was diluted with water to have a particulate cellulose concentration of 0.05% by weight. The maximum viscosity value ($\eta$max) of sample S12 at 25° C. was $1 \times 10^7$ mPa·s.

(Evaluation)

Sample S12 was examined with respect to the state of spray, unevenness in spray coating, and anti-dripping properties (after spraying). As a result, it was found that sample S12 exhibited excellent properties (evaluation symbol ◯) in all these items of evaluation. Further, it was found that sample S12 was homogeneous and exhibited no phase separation for a long time (for 3 months at 30° C.), showing that sample S12 had high stability. In order to confirm the safety of the gel-like composition, an experiment was conducted as follows. Sample S12 was sprayed over an upper arm of each of 10 healthy volunteers, and a closed patch test was performed for 24 hours to investigate whether or not a skin irritation was caused by the sprayed gel-like composition. The results of the test were classified into the following three degrees: ◯=no irritation was caused, Δ=slight irritation, if any, was caused (or difficult to judge), and X=irritation was caused. As a result, it was found that with respect to all of the 10 persons, the test results were: ◯=no irritation was caused, thereby confirming the high safety of the gel-like composition. Further, the gel-like composition was sprayed onto the face of each of the above-mentioned 10 healthy volunteers, in order to survey what sensation was produced in the 10 persons immediately after the spraying. In a questionnaire performed after the spraying, all 10 persons answered that they got excellent sensation, i.e., a smooth and refreshing feel.

EXAMPLE 13

Using the above-mentioned sample A, a spray pack was produced containing an emollient lotion spraying composition which serves as a moisturizing emollient emulsion, wherein the spraying composition had the following formulation:

| | |
|---|---|
| cetyl alcohol (oil component): | 1.0% by weight |
| beeswax (oil component): | 0.5% by weight |
| vaseline (oil component): | 2.0% by weight |
| squalane (oil component): | 6.0% by weight |
| dimethylpolysiloxane (oil component): | 2.0% by weight |
| ethanol: | 5.0% by weight |
| glycerol (humectant): | 2.0% by weight |
| 1,3-butylen glycol (humectant): | 3.0% by weight |
| polyethylene glycol (10) monooleate (surfactant): | 0.5% by weight |
| glycerol monostearate (surfactant): | 1.0% by weight |
| an antiseptic agent and a perfume: | appropriate amounts |
| sample A: | 30.0% by weight |
| purified water: | 29.0% by weight |

(Production Method)

The humectants were added to purified water, and the resultant aqueous mixture was stirred at a revolution rate of 7,000 rpm by means of a homomixer (T.K. ROBO MICS™, manufactured and sold by Tokushu Kika Kogyo Co., Ltd., Japan) while heating until the temperature of the aqueous mixture reached 70° C. On the other hand, the surfactant and antiseptic agent were added to the oil components, and the resultant oily mixture was heated to 70° C. The oily mixture at 70° C. was added to the aqueous mixture in the homomixer while stirring, thereby effecting a preliminary emulsification, thereby obtaining a preliminary emulsion. The revolution rate of the homomixer was changed to 9,000 rpm and then sample A and ethanol were added to the preliminary emulsion, and the resultant was subjected to a treatment for dispersing, at a revolution rate of 9,000 rpm for 10 minutes, thereby obtaining a white gel-like liquid. The obtained white gel-like liquid was then subjected to deaeration and filtration and then cooled, thereby obtaining a spraying composition. The obtained composition was packed in a 50 ml volume dispenser type spray container device (manufactured and sold by SANPLATEC Corp., Japan). The obtained composition is hereinafter referred to as "sample S13". The transmittance of sample S13 to visible rays having a wavelength of 660 nm was 2%, as measured in the state in which sample S13 was diluted with water to have a particulate cellulose concentration of 0.05% by weight. The maximum viscosity value ($\eta_{max}$) of sample S13 at 25° C. was $3 \times 10^6$ mPa·s.

(Evaluation)

Sample S13 was examined with respect to the state of spray, unevenness in spray coating, and anti-dripping properties (after spraying). As a result, it was found that sample S13 exhibited excellent properties (evaluation symbol ◯) in all these items of evaluation. Further, it was found that sample S13 was homogeneous and exhibited no phase separation for a long time (for 3 months at 30° C.), showing that sample S13 had high stability. In order to confirm the safety of sample S13, an experiment was conducted as follows. Sample S13 was sprayed over an upper arm of each of 10 healthy volunteers, and a closed patch test was performed for 24 hours to investigate whether or not a skin irritation was caused by the sprayed gel-like composition. The results of the test were classified into the following three degrees: ○=no irritation was caused, Δ=slight irritation, if any, was caused (or difficult to judge), and X=irritation was caused. As a result, it was found that with respect to 9 persons, the test results were: ○=no irritation was caused, and 1 person gave test results such that the evaluation symbol was Δ, thereby confirming the high safety of the gel-like composition.

Further, the gel-like composition was sprayed onto the face of each of the above-mentioned 10 healthy volunteers, in order to survey what sensation was produced in the 10 persons immediately after the spraying. In a questionnaire performed after the spraying, all 10 persons answered that they got excellent sensation, i.e., a smooth and refreshing feel.

EXAMPLE 14 AND COMPARATIVE EXAMPLE 9

Using the above-mentioned sample A, a spray pack was produced in which an aerosol shaving foam spraying composition having the below-mentioned formulation (1) was packed in accordance with the below-mentioned packing formulation (2).

(1) Formulation of the Spraying Composition

| | |
|---|---|
| stearic acid (oil component): | 4.5% by weight |
| coconut oil fatty acid (oil component): | 1.5% by weight |
| glycerin monostearate (surfactant): | 5.0% by weight |
| glycerol (humectant): | 10.0% by weight |
| triethanolamine (alkali) | 4.0% by weight |
| perfume: | an appropriate amount |
| sample A: | 25.0% by weight (for Example 14) |
| sample A: | not added (for Comparative Example 9) |
| purified water: | 50.0% by weight (for Example 14) |
| purified water: | 75.0% by weight (for Comparative Example 9) |

(2) Packing Formulation (Common to the Example and Comparative Example)

| | |
|---|---|
| spraying composition: | 96.0% by weight |
| LPG (propellant gas): | 4.0% by weight |

(Production Method)

Glycerol and triethanolamine were added to purified water, and the resultant aqueous mixture (aqueous phase) was heated to and maintained at 70° C. On the other hand, the remainder of the above-mentioned ingredients were mixed together and heated, and the resultant oily mixture (oil phase) was heated to and maintained at 70° C. The obtained oil phase was added to the obtained aqueous phase, and the resultant mixture was subjected to a treatment for reaction and emulsification, by stirring at a revolution rate of 8,000 rpm by means of a homomixer (T.K. ROBO MICS™, manufactured and sold by Tokushu Kika Kogyo Co., Ltd., Japan). The resultant emulsion was cooled to 30° C. Then, only in the case of Example 14, sample A was added to the emulsion while stirring at a revolution rate of 8,000 rpm, and the resultant mixture was subjected to a treatment for dispersing for 10 minutes, thereby obtaining an emulsion. In both of the Example and Comparative Example, the obtained emulsions were individually subjected to deaeration and filtration, thereby obtaining white viscous emulsified compositions. Each of the obtained compositions was individually packed in an aerosol container device in an amount as specified above, and a valve was fitted on the container device, and then the propellant gas in an amount as specified above was introduced in the container device, to thereby obtain an aerosol spray pack. The spraying compositions obtained in Example 14 and Comparative Example 9 are hereinafter referred to as "sample S14" and "sample H9", respectively. The transmittances of samples S14 (containing cellulose) and H9 (containing no cellulose) to visible rays having a wavelength of 660 nm were both less than 1%, as measured in the state in which the samples were diluted with water to have oil concentrations which are the same with respect to both of the samples, wherein sample S14 has a particulate cellulose concentration of 0.05% by weight. The maximum viscosity values ($\eta_{max}$) of samples S14 and H9 at 25° C. were $2\times10^6$ mPa·s (S14) and $5\times10^3$ mPa·s (H9).

(Evaluation)

When samples S14 and H9 were evaluated with respect to the spraying properties thereof, both samples produced a good foam. 5 Minutes after the spraying, a comparison was made between the volumes of the two foams produced from the samples. It was found that the volume of the foam produced from sample H9 had reduced to a volume which is less than ½ of the original volume thereof, whereas the foam produced from sample S14 retained its volume as measured immediately after the spraying. Thus, it was shown that the foam obtained in Example 14 exhibits an extremely high retention. Both samples exhibited an excellent fixation to the skin surface. It was also found that the spraying properties of both samples were stable for a long time (for 3 months at 30° C.). Further, an experiment was performed in which each of these samples was individually sprayed onto the chin of each of 10 healthy volunteers and the resultant foam was used as a shaving foam, in order to survey what sensation was produced in the 10 persons using the shaving foam. In a questionnaire performed after the experiment, all 10 persons answered that the foam produced from sample S14 gave excellent sensation, and 7 persons answered that the foam produced from sample H9 gave excellent sensation. Thus, it was found that sample S14 is superior to sample H9 in the retention of foam and the sensation produced when used.

EXAMPLE 15

Using the above-mentioned sample A, a spray pack was produced in which an aerosol nonsteroidal anti-inflammatory analgesic spraying composition having the below-mentioned formulation (1) was packed in accordance with the below-mentioned packing formulation (2).

(1) Formulation of the Spraying Composition

| | |
|---|---|
| ketoprofen (active ingredient): | 0.3% by weight |
| ethanol: | 30.0% by weight |
| propylene glycol (water-soluble additive): | 1.0% by weight |
| cetyl alcohol (oil component): | 0.5% by weight |
| palmitic acid (oil component): | 0.5% by weight |
| isopropyl myristate (oil component): | 0.1% by weight |
| dimethylpolysiloxane (oil component): | 0.1% by weight |
| polyoxyethylene(50)-hardened castor oil (surfactant): | 0.2% by weight |
| citric acid (pH adjustor): | 0.06% by weight |
| sample A: | 18.8% by weight |
| purified water: | 48.4% by weight |

(2) Packing Formulation

| | |
|---|---|
| spraying composition: | 50.0% by weight |
| LPG (propellant gas): | 50.0% by weight |

(Production Method)

Purified water was added to sample A. The resultant mixture was subjected to a treatment for dispersing, at a revolution rate of 7,000 rpm by means of a homomixer (T.K. ROBO MICS™, manufactured and sold by Tokushu Kika Kogyo Co., Ltd., Japan), and the water-soluble additive was added to and dissolved in the mixture while effecting the treatment for dispersing, followed by a further treatment for dispersing for 10 minutes, thereby obtaining a slightly viscous transparent dispersion. On the other hand, the surfactant, oil components and active ingredient were dissolved into ethanol, and the resultant solution was added to the above-mentioned transparent dispersion, and the resultant mixture was subjected to a microemulsification at a revolution rate of 10,000 rpm by means of the homomixer, followed by deaeration and filtration, thereby obtaining a highly transparent, viscous composition. The obtained composition was packed in an aerosol container device in an amount as specified above, and a valve was fitted on the container device, and the propellant gas in an amount as specified above was introduced into the container device, to thereby obtain an aerosol spray pack. The spraying composition obtained in Example 15 is hereinafter referred to as "sample S15". The transmittance of sample S15 to visible rays having a wavelength of 660 nm was 84%, as measured in the state in which sample S12 was diluted with water to have a particulate cellulose concentration of 0.05% by weight. The maximum viscosity value ($\eta_{max}$) of sample S15 at 25° C. was $8\times10^3$ mPa·s.

(Evaluation)

Sample S15 was examined with respect to the state of spray, unevenness in spray coating, and anti-dripping properties (after spraying). As a result, it was found that sample S15 exhibited excellent properties (evaluation symbol ◯) in all these items of evaluation. Further, it was found that sample S15 exhibited substantially the same excellent properties even after it was stored for a long time (for 3 months at 30° C.), showing that sample S15 had high storage stability. Further, an experiment was performed for 10 days, in which 10 healthy persons perform an exercise every day, and sample S15 was used by the 10 healthy persons after the exercise in order to survey the sensation produced immediately after the spraying of sample S15 as well as the anti-inflammatory effects of sample S15 on the muscles. After the 10-day experiment, a questionnaire was given. In the questionnaire, all 10 persons answered that they got excellent sensation, i.e., a smooth and refreshing feel, and 8 persons answered that the anti-inflammatory effects of sample S15 were very high.

EXAMPLE 16

Using the above-mentioned sample A, a spray pack was produced comprising a trigger type container device and, packed therein, a detergent spraying composition having the following formulation:

| | |
|---|---|
| polyoxyethylene(13)nonyl phenyl ether (surfactant): | 5.0% by weight |
| ethanol: | 5.0% by weight |
| antiseptic agent: | an appropriate amount |
| sample A: | 37.5% by weight |
| purified water: | 52.5% by weight |

(Production Method)

Purified water was added to sample A. The resultant mixture was subjected to a treatment for dispersing, at a revolution rate of 7,000 rpm for 10 minutes by means of a homomixer (T.K. ROBO MICS™, manufactured and sold by Tokushu Kika Kogyo Co., Ltd., Japan), and the surfactant was added to the mixture, and then ethanol having the antiseptic agent dissolved therein was added thereto, followed by a further treatment for dispersing for 10 minutes. Thereafter, the resultant mixture was subjected to deaeration and filtration, thereby obtaining a transparent gel-like composition. The obtained composition was packed in a 500 ml volume trigger type spray container device (CANIONSPRAY™, manufactured and sold by SANPLATEC Corp., Japan). The obtained composition is hereinafter referred to as "sample S16". The transmittance of sample S16 to visible rays having a wavelength of 660 nm was 92%, as measured in the state in which sample S16 was diluted with water to have a particulate cellulose concentration of 0.05% by weight. The maximum viscosity value ($\eta_{max}$) of sample S16 at 25° C. was $3\times10^6$ mPa·s.

(Evaluation)

Sample S16 was examined with respect to the state of spray, unevenness in spray coating, and anti-dripping properties (after spraying). As a result, it was found that sample S16 exhibited excellent properties (evaluation symbol ◯) in all these items of evaluation. Further, it was found that sample S16 was homogeneous and exhibited no phase separation for a long time (for 3 months at 30° C.), showing that sample S16 had high stability.

Further, the following experiment was performed. A vertical surface of a fixed porcelain (specifically, a urinal) was stained with an oily substance. Sample S16 was sprayed onto the stain on the vertical surface of the porcelain, and then the sprayed composition and the stain were wiped off with a cloth. As a result, the excellent cleaning effect of sample S16 was confirmed. Further, it was found that, after the wiping off, the particulate cellulose of sample S16 did not remain on the porcelain surface and, hence, the porcelain surface did not lose its luster at all. In view of these results, it is presumed that the cellulose (which is amphiphilic) in the composition quite effectively functions for facilitating the cleaning mechanism that water and the surfactant engulf and remove the stain substance.

TABLE 1

| Sample | Thickening agent (Concentration (% by weight) | State of spray | Unevenness in spray coating | Anti-dripping properties | Coating formation ability |
|---|---|---|---|---|---|
| S1 | cellulose (0.5) | ○ | ○ | △ | ○ |
| S2 | cellulose (1.0) | ○ | ○ | ○ | ○ |
| S3 | cellulose (1.5) | ○ | ○ | ○ | ○ |
| S4 | cellulose (2.0) | ○ | ○ | ○ | ○ |
| S5 | cellulose (4.0) | ○ | △ | △ | ○ |
| S6 | cellulose (2.0) | ○ | △ | △ | ○ |
| S7 | cellulose (2.0) | ○ | △ | △ | ○ |
| H1 | cellulose (5.0) | X | X | X | X |
| H2 | Carbopol 940 ™ (0.5) | X | cannot be evaluated | cannot be evaluated | X |
| H3 | Carbopol 940 ™ (1.5) | X | cannot be evaluated | cannot be evaluated | X |
| H4 | polyacrylamide (0.5) | △ | X | X | X |
| H5 | polyacrylamide (1.5) | X | cannot be evaluated | cannot be evaluated | X |
| H6 | Smecton SA2 ™ (0.5) | ○ | ○ | △ | X |
| H7 | Smecton SA2 ™ (1.5) | ○ | ○ | △ | X |

TABLE 2

| Sample | State of spray | Unevenness in spray coating | Anti-dripping properties |
|---|---|---|---|
| S8 | ○ | ○ | ○ |
| H8 | ○ | △ | △ |

INDUSTRIAL APPLICABILITY

The spraying composition used in the present invention is advantageous not only in that it has excellent spraying properties but also, after the spraying, the sprayed composition (coating) has excellent properties with respect to fixation to the surface coated, anti-dripping properties, spreadability and finish (uniformity of the coating). Therefore, the spray pack of the present invention can be used in a wide variety of fields, such as the fields of skincare products, hair care products, a medicine for external use, a medicine for oral use, an insecticide, a fragrance, a deodorizer, an antimicrobial agent, a sterilizer, a halitosis deodorizer, a detergent, a paint, a coating agent for anti-fogging treatment, a coating agent for anti-static treatment, and an antiseptic agent. By appropriately adjusting the formulation of the composition, it is possible to provide a foamable spraying composition capable of producing a foam having very high stability (very high retention) and provide a spraying composition having very high safety. Further, by appropriately selecting the liquid dispersion medium and other components of the composition, as long as the selection is made so as not to spoil the excellent effects of the composition, it is possible to provide not only spraying compositions having conventional formulations, but also spraying compositions having a wide variety of new aqueous formulations.

The invention claimed is:

1. A spray pack for use in forming a uniform, stable spray coating, comprising a spray container device and, packed therein, a spraying composition comprising a liquid dispersion medium and, dispersed therein, particulate cellulose having an average degree of polymerization (DP) of not more than 300 and an average particle diameter of not more than 10 μm,
   said spraying composition having a cellulose content of from 0.1 to 5.0% by weight,
   wherein said spraying composition exhibits a maximum viscosity value ($\eta_{max}$) of $1\times10^3$ mPa·s or more in the viscosity-shear stress curve obtained, with respect to said composition, using a cone-plate type rotating viscometer in a shear rate region of from $1\times10^{-3}$ s$^{-1}$ to $1\times10^2$ s$^{-1}$ and at 25° C.

2. The spray pack according to claim 1, wherein said particulate cellulose has an average degree of polymerization (DP) of not more than 100, and has a cellulose I type crystal component fraction of 0.1 or less and a cellulose II type crystal component fraction of 0.4 or less, and wherein said particulate cellulose has an average particle diameter of not more than 2 μm.

3. The spray pack according to claim 1 or 2, wherein said particulate cellulose has an average particle diameter of not more than 1 μm.

4. The spray pack according to claim 1 or 2, wherein said maximum viscosity value ($\eta_{max}$) in the viscosity-shear stress curve is $5\times10^5$ mPa·s or more.

5. The spray pack according to claim 1 or 2, wherein said liquid dispersion medium comprises water and an organic solvent.

6. The spray pack according to claim 5, wherein said organic solvent is a water-soluble alcohol.

7. The spray pack according to claim 1 or 2, which further comprises at least one functional additive.

8. The spray pack according to claim 7, wherein at least a part of said functional additive is an ionic compound, and wherein the content of said ionic compound in said composition is from 0.1 to 10% by weight.

9. The spray pack according to claim 7, wherein said at least one functional additive is selected from the group consisting of an oil compound, a humectant, a surfactant, a metal oxide, an ultraviolet screener, an inorganic salt, a metal powder, a gum, a dye, a pigment, a silica compound, a latex, a water-soluble polymer, an amino acid, a cosmetic ingredient, a pharmaceutical, an insecticide, a deodorizer, an antimicrobial agent, an antiseptic agent and a perfume.

10. The spray pack according to claim 1 or 2, wherein when said spraying composition is diluted with water to have a particulate cellulose concentration of 0.05% by weight, the resultant aqueous composition exhibits a transmittance of 80% or more to visible rays having a wavelength of 660 nm.

11. A method for forming a uniform, stable spray coating, comprising:
   providing a spray pack comprising a spray container device and, packed therein, a spraying composition, and
   actuating said spray container device to spray said spraying composition onto a surface, thereby forming a spray coating on said surface,
   said spraying composition comprising a liquid dispersion medium and, dispersed therein, particulate cellulose having an average degree of polymerization (DP) of not more than 300 and an average particle diameter of not more than 10 μm,
   said spraying composition having a cellulose content of from 0.1 to 5.0% by weight,
   wherein said spraying composition exhibits a maximum viscosity value ($\eta_{max}$) of $1\times10^3$ mPa·s or more in the viscosity-shear stress curve obtained, with respect to said composition, using a cone-plate type rotating viscometer in a shear rate region of from $1\times10^{-3}$ s$^{-1}$ to $1\times10^{2}$ s$^{-1}$ and at 25° C.

12. The method according to claim 11, wherein said particulate cellulose has an average degree of polymerization (DP) of not more than 100, and has a cellulose I type crystal component fraction of 0.1 or less and a cellulose II type crystal component fraction of 0.4 or less, and wherein said particulate cellulose has an average particle diameter of not more than 2 μm.

13. The method according to claim 11 or 12, wherein said particulate cellulose has an average particle diameter of not more than 1 μm.

14. The method according to claim 11 or 12, wherein said maximum viscosity value ($\eta_{max}$) in the viscosity-shear stress curve is $5\times10^{5}$ mPa·s or more.

15. The method according to claim 11 or 12, wherein said liquid dispersion medium comprises water and an organic solvent.

16. The method according to claim 15, wherein said organic solvent is a water-soluble alcohol.

17. The method according to claim 11 or 12, which further comprises at least one functional additive.

18. The method according to claim 17, wherein at least a part of said functional additive is an ionic compound, and wherein the content of said ionic compound in said composition is from 0.1 to 10% by weight.

19. The method according to claim 17, wherein said at least one functional additive is selected from the group consisting of an oil compound, a humectant, a surfactant, a metal oxide, an ultraviolet screener, an inorganic salt, a metal powder, a gum, a dye, a pigment, a silica compound, a latex, a water-soluble polymer, an amino acid, a cosmetic ingredient, a pharmaceutical, an insecticide, a deodorizer, an antimicrobial agent, an antiseptic agent and a perfume.

20. The method according to claim 11 or 12, wherein when said spraying composition is diluted with water to have a particulate cellulose concentration of 0.05% by weight, the resultant aqueous composition exhibits a transmittance of 80% or more to visible rays having a wavelength of 660 nm.

* * * * *

UNITED STATES PATENT AND TRADEMARK OFFICE
CERTIFICATE OF CORRECTION

PATENT NO. : 7,094,448 B2
APPLICATION NO. : 10/330920
DATED : August 22, 2006
INVENTOR(S) : Hirofumi Ono et al.

It is certified that error appears in the above-identified patent and that said Letters Patent is hereby corrected as shown below:

Title Page, Item (73) Assignee: "Asahi Kasei Chemical Corporation" should be changed to --Asahi Kasei Chemicals Corporation--.

Column 1, line 46, "general purpose" should be changed to --general-purpose--.

Column 2, line 9, "by some degree" should be changed to --to some extent--.

Column 4, line 2, "general purpose" should be changed to --general-purpose--.

Column 6, line 7, "$1 \times 10^{-3} \, s^{-3}$" should be changed to --$1 \times 10^{-3} \, s^{-1}$--.

Column 12, line 2, "general purpose" should be changed to --general-purpose--.

Column 14, line 48, "preferably" should be changed to --more advantageously--.

Column 15, line 10, "preferably" should be changed to --more advantageously--.

Column 15, line 27, "preferably" should be changed to --more advantageously--.

Column 16, line 50, "preferably" should be changed to --more advantageously--.

Column 20, line 22, "Lobo. mics$^{TM}$" should be changed to --ROBO MICS$^{TM}$--.

Column 34, line 36, "with" should be changed to --With--.

Signed and Sealed this

Fourteenth Day of August, 2007

JON W. DUDAS
*Director of the United States Patent and Trademark Office*